US010123971B2

(12) United States Patent
Patel et al.

(10) Patent No.: US 10,123,971 B2
(45) Date of Patent: *Nov. 13, 2018

(54) HETEROGENEOUS IMPLANTABLE DEVICES FOR DRUG DELIVERY

(71) Applicant: Titan Pharmaceuticals, Inc., South San Francisco, CA (US)

(72) Inventors: Rajesh A. Patel, Redwood City, CA (US); Sunil R. Bhonsle, Oakland, CA (US)

(73) Assignee: Titan Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/802,504

(22) Filed: Mar. 13, 2013

(65) Prior Publication Data

US 2013/0195950 A1  Aug. 1, 2013

Related U.S. Application Data

(63) Continuation of application No. 13/634,535, filed as application No. PCT/US2011/028727 on Mar. 16, 2011.

(60) Provisional application No. 61/314,465, filed on Mar. 16, 2010.

(51) Int. Cl.
| | |
|---|---|
| *A61K 9/00* | (2006.01) |
| *A61K 47/32* | (2006.01) |
| *A61K 31/485* | (2006.01) |
| *A61K 31/198* | (2006.01) |
| *A61K 31/4045* | (2006.01) |
| *A61K 45/06* | (2006.01) |
| *A61K 9/20* | (2006.01) |
| *A61K 9/28* | (2006.01) |

(52) U.S. Cl.
CPC .......... *A61K 9/0024* (2013.01); *A61K 31/198* (2013.01); *A61K 31/4045* (2013.01); *A61K 31/485* (2013.01); *A61K 45/06* (2013.01); *A61K 47/32* (2013.01); *A61K 9/2086* (2013.01); *A61K 9/2886* (2013.01)

(58) Field of Classification Search
None
See application file for complete search history.

(56) References Cited

U.S. PATENT DOCUMENTS

| | | |
|---|---|---|
| 3,337,665 A | 8/1967 | Underwood et al. |
| 3,625,214 A * | 12/1971 | Higuchi ......................... 424/424 |
| 3,880,691 A | 4/1975 | Pannenbecker et al. |
| 3,920,805 A * | 11/1975 | Roseman ....................... 424/432 |
| 3,926,188 A | 12/1975 | Baker et al. |
| 4,191,741 A | 3/1980 | Hudson et al. |
| 4,379,117 A | 4/1983 | Baird, Jr. et al. |
| 4,693,886 A | 9/1987 | Ayer |
| 4,832,589 A | 5/1989 | Gini et al. |
| 4,883,666 A | 11/1989 | Sabel et al. |
| 5,063,018 A | 11/1991 | Fontirroche et al. |
| 5,114,719 A | 5/1992 | Sabel et al. |
| 5,601,835 A | 2/1997 | Sabel et al. |
| 5,683,719 A | 11/1997 | Newton |
| 5,733,565 A | 3/1998 | Moo-Young et al. |
| 6,086,908 A | 7/2000 | Göpferich |
| 6,117,441 A | 9/2000 | Moo-Young et al. |
| 6,258,121 B1 | 7/2001 | Yang et al. |
| 6,506,437 B1 | 1/2003 | Harish et al. |
| 7,364,748 B2 | 4/2008 | Claude |
| 7,384,660 B2 | 6/2008 | Hossainy et al. |
| 7,736,665 B2 | 6/2010 | Patel et al. |
| 8,845,716 B2 | 9/2014 | Lee et al. |
| 8,852,623 B2 | 10/2014 | Patel et al. |
| 2003/0059471 A1 | 3/2003 | Compton et al. |
| 2005/0031667 A1 | 2/2005 | Patel et al. |
| 2005/0031668 A1* | 2/2005 | Patel et al. ................... 424/426 |
| 2007/0190111 A1 | 8/2007 | Robinson et al. |
| 2007/0275031 A1 | 11/2007 | Patel et al. |
| 2007/0280992 A1 | 12/2007 | Margaron et al. |
| 2008/0026031 A1 | 1/2008 | Patel et al. |
| 2009/0022806 A1* | 1/2009 | Mousa et al. .................. 424/489 |
| 2009/0081278 A1* | 3/2009 | De Graaff et al. ........... 424/430 |
| 2010/0015200 A1 | 1/2010 | McClain et al. |
| 2013/0189342 A1 | 7/2013 | Patel et al. |
| 2013/0195951 A1 | 8/2013 | Patel et al. |
| 2013/0202673 A1 | 8/2013 | Patel et al. |

FOREIGN PATENT DOCUMENTS

| | | |
|---|---|---|
| DE | 196 08 423 A1 | 9/1997 |
| EP | 0 009 410 A2 | 4/1980 |

(Continued)

OTHER PUBLICATIONS

Final Office Action dated Aug. 29, 2014 for U.S. Appl. No. 13/634,535 filed on Mar. 16, 2011 (Int'l), 18 pages.

(Continued)

*Primary Examiner* — Jessica Worsham
(74) *Attorney, Agent, or Firm* — Morrison & Foerster LLP

(57) ABSTRACT

The present invention comprises compositions, methods and kits for delivering drugs. The invention provides an implantable device for delivery of a pharmaceutical substance to a patient, comprising a core comprising a core polymeric material optionally containing a core pharmaceutical substance, surrounded by a first layer comprising a first-layer pharmaceutical substance and a first-layer polymeric material, optionally surrounded by one or more additional layers comprising an additional pharmaceutical substance and an additional polymeric material, where the core, first, and optional additional polymeric materials may be the same or different, and where the optional core pharmaceutical substance, first-layer pharmaceutical substance, and optional additional pharmaceutical substances are the same or different. Implantation of the device allows a controlled release of drug for an extended period of time. The device may be implanted subcutaneously in an individual in need of continuous treatment with a drug.

12 Claims, 4 Drawing Sheets

(56) References Cited

FOREIGN PATENT DOCUMENTS

| | | |
|---|---|---|
| EP | 0 009 410 A3 | 4/1980 |
| EP | 1 084 703 A1 | 3/2001 |
| EP | 1084703 A1 * | 3/2001 |
| GB | 1522735 A | 8/1978 |
| JP | 51-133411 A | 11/1976 |
| JP | 55-045694 A | 3/1980 |
| JP | 61-249916 A | 11/1986 |
| JP | 2000-507218 A | 6/2000 |
| JP | 2005-507925 A | 3/2005 |
| JP | 2005-528422 A | 9/2005 |
| KR | 10-0511618 B1 | 8/2005 |
| WO | WO-1997/02015 A1 | 1/1997 |
| WO | WO-2003/037244 A2 | 5/2003 |
| WO | WO-2003/101358 A1 | 12/2003 |
| WO | WO-2008/062008 A1 | 5/2008 |
| WO | WO-2009/036999 A1 | 3/2009 |
| WO | WO-2010/105995 A2 | 9/2010 |
| WO | WO-2010/105995 A3 | 9/2010 |
| WO | WO-2011/116132 A1 | 9/2011 |

OTHER PUBLICATIONS

Kleppner, S.R. et al. (Mar. 2006). "In-vitro and In-vivo Characterization of a Buprenorphine Delivery System," *Journal of Pharmacy and Pharmacology* 58(3):295-302.

"Nalmefene," located at <http://www.thefreedictionary.com/nalmefene>, last visited on Feb. 3, 2014, 1 page.

International Preliminary Report on Patentability dated Sep. 18, 2012 for PCT Patent Application No. PCT/US2011/028727 filed Mar. 16, 2011, 6 pages.

International Search Report dated May 6, 2011 for PCT Patent Application No. PCT/US11/28727 filed Mar. 16, 2011, 2 pages.

Written Opinion dated May 6, 2011 for PCT Patent Application No. PCT/US11/28727 filed Mar. 16, 2011, 5 pages.

European Extended Search Report dated Mar. 18, 2014 for EP Patent Application No. 11756957.4 filed Mar. 16, 2011, 9 pages.

Non-Final Office Action dated Feb. 10, 2014 for U.S. Appl. No. 13/634,535 filed Mar. 1, 2013, 13 pages.

Response to Non-Final Office Action submitted to the USPTO dated May 12, 2014 for U.S. Appl. No. 13/634,535, filed Mar. 1, 2013, 17 pages.

Interview Summary dated June 13, 2014 for U.S. Appl. No. 13/634,535, filed Mar. 1, 2013, 3 pages.

Non-Final Office Action dated Feb. 10, 2014 for U.S. Appl. No. 13/802,526, filed Mar. 13, 2013, 13 pages.

Non-Final Office Action dated Feb. 10, 2014 for U.S. Appl. No. 13/802,539, filed Mar. 13, 2013, 13 pages.

Final Office Action dated Nov. 20, 2014 for U.S. Appl. No. 13/802,526, filed Mar. 13, 2013, 18 pages.

Final Office Action dated Nov. 20, 2014 for U.S. Appl. No. 13/802,539, filed Mar. 13, 2013, 19 pages.

Non-Final Office Action dated Jul. 24, 2015, for U.S. Appl. No. 13/634,535, filed Mar. 1, 2013, 11 pages.

U.S. Final Office Action dated Dec. 24, 2015, for U.S. Appl. No. 13/634,535, filed Mar. 1, 2013, 11 pages.

U.S. Non-Final Office Action dated Feb. 13, 2017 for U.S. Appl. No. 13/634,535 filed Mar. 1, 2013, 14 pages.

Singaporean Search Report and Written Opinion dated Aug. 21, 2017 for SG Application No. 10201501964Q filed on Mar. 13, 2015, eleven pages.

U.S. Final Office Action dated Sep. 8, 2017, for U.S. Appl. No. 13/634,535, filed Mar. 1, 2013, 13 pages.

U.S. Notice of Allowance dated Mar. 30, 2018, for U.S. Appl. No. 13/634,535, filed Mar. 1, 2013, 9 pages.

* cited by examiner

HETEROGENEOUS IMPLANTABLE DEVICES FOR DRUG DELIVERY

CROSS REFERENCE TO RELATED APPLICATIONS

This patent application is a continuation of U.S. patent application Ser. No. 13/634,535, which is a national stage filing of International Patent Application No. PCT/US2011/028727 having an International Filing Date of Mar. 16, 2011, which claims priority benefit of U.S. Provisional Patent Application No. 61/314,465, filed Mar. 16, 2010. The entire contents of those applications are hereby incorporated by reference herein.

TECHNICAL FIELD

The invention provides implantable devices comprising a core comprising a core polymeric material and an optional core pharmaceutical substance, surrounded by one or more layers comprising a first-layer and additional polymeric materials (which may or may not be identical to the first) and a pharmaceutical substance or substances.

BACKGROUND OF THE INVENTION

Many patients require long-term, regular dosing with drugs or pharmaceutical substances, including substances for pain control. Effective treatment often necessitates the ingestion of multiple tablets per day. Compliance with this dosing scheme is often difficult. Furthermore, enteral drug delivery is sometimes poorly tolerated or prohibited in patients with particular indications. In addition, oral tablets may be subject to abuse or other illicit use. Oral and sublingual delivery can result in plasma concentrations of drug peaking quickly and dropping steeply. Continuous parenteral delivery of drug substances is expensive, cumbersome and dependent on the availability of refrigeration, catheters, pumps and trained personnel. These methods can result in poor patient compliance with dosing regimes. Thus, there is a need for devices which regularly dose patients with drug substances.

Implantable devices may be used for drug delivery. These devices can produce long-term delivery of drugs, ensuring compliance independent of the patient, maintaining stable plasma levels of medication and reducing the likelihood of abuse or diversion.

Continuous release of a compound in vivo over an extended duration may be achieved via implantation of a device containing the compound encapsulated in a polymeric matrix. Examples of implantable polymeric devices for continuous drug release are described in, e.g., U.S. Pat. Nos. 4,883,666; 5,114,719; and 5,601,835. Patel et al. U.S. Patent Application Publication Nos. 2004/0033250, 2007/0275031, and 2008/0026031, and Kleppner et al. 2006 J. Pharm. Pharmacol. 58:295-302 describe an implantable device comprising buprenorphine blended with ethylene vinyl acetate (EVA copolymer). Patel et al. U.S. Patent Application Publication No. 2005/0031668 describes an implantable polymeric device for sustained release of nalmefene. Patel et al. U.S. Patent Application Publication No. 2005/0031667 describes an implantable polymeric device for sustained release of dopamine agonists. Additional drug delivery devices include stents coated with compositions comprising drugs. Various devices and coatings are described in U.S. Pat. No. 6,506,437 to Harish; U.S. Pat. No. 7,364,748 to Claude and U.S. Pat. No. 7,384,660 to Hossainy. U.S. Pat. No. 3,625,214 describes a drug-delivery device for prolonged drug delivery, fabricated in a spiral or "jellyroll" fashion. U.S. Pat. No. 3,926,188 describes a three-layer laminate drug dispenser comprising a core lamina of a crystalline drug of low water solubility dispersed in a polymer matrix, interposed between outer laminas made of a drug release rate controlling polymer. U.S. Pat. No. 5,683,719 describes a controlled release composition comprising an extruded core of active material and excipients, the core being coated in a water insoluble coating.

Implantable devices are inserted subcutaneously in areas of the body, and may be subject to physical damage. Kleppner et al. 2006 J. Pharm. Pharmacol. 58:295-302 described breakage of devices within the bodies of treated dogs. Implantable devices comprising EVA (ethyl vinyl acetate copolymer) and buprenorphine (for treatment of opioid dependence) were inserted subcutaneously in the backs of test dogs. 70% of the implants had broken within 10 months. Drug delivery was estimated to increase by 5% in implants that broke into two pieces, and 10% in implants that broke into three pieces. Thus, breakage of implantable devices would interfere with the regulated dosing and delivery of drug substances. Breakage of the implantable devices may also result in jagged device edges which could cause tissue damage and pain to the patient. Finally, breakage of the implantable devices seriously complicates removal of the device, as it may be difficult to extract the broken pieces without causing damage to the surrounding tissue.

There is a need for implantable devices which are not subject to breakage within the body of the patient.

BRIEF SUMMARY OF THE INVENTION

The invention provides implantable drug delivery devices of heterogeneous composition. Various embodiments of the devices can provide enhanced mechanical strength and/or advantageous drug delivery properties.

In one embodiment, the invention encompasses an implantable device for delivery of a pharmaceutical substance to a patient, comprising a core comprising a core polymeric material, where the core optionally comprises a core pharmaceutical substance, surrounded by a first layer comprising a first-layer pharmaceutical substance and a first-layer polymeric material, optionally surrounded by one or more additional layers comprising an additional pharmaceutical substance and an additional polymeric material, where the core, first-layer, and additional polymeric materials may be the same or different, and where the core, first-layer, and additional pharmaceutical substances are the same or different. In one embodiment, the core does not have a core pharmaceutical substance. In another embodiment, the core does have a core pharmaceutical substance.

In one embodiment, the device is generally rod-shaped and comprises a core comprising a core polymeric material, where the core optionally comprises a core pharmaceutical substance, surrounded by one or more layers comprising a first-layer polymeric material, and, if more than one layer is present, a second-layer polymeric material, a third-layer polymeric material, through an Nth-layer polymeric material when N layers are present (where N is a positive integer), where said layer or layers may or may not be identical to the core polymer, and where each layer comprises a pharmaceutical substance. The core and layers can comprise the same pharmaceutical substance. The core and layers can all comprise different pharmaceutical substances. In one embodiment, the core does not have a core pharmaceutical substance. In another embodiment, the core does have a core pharmaceutical substance.

In one embodiment, the invention encompasses an implantable device for delivery of a pharmaceutical substance to a patient, comprising: a core comprising a core polymeric material, where the core optionally comprises a core pharmaceutical substance; and a first layer comprising a first-layer pharmaceutical substance and a first-layer polymeric material surrounding the core; and optionally comprising one or more additional layers comprising an additional pharmaceutical substance and an additional polymeric material, where the core, first-layer, and any additional polymeric materials are the same or different, and where the core, first and any additional pharmaceutical substances are the same or different. In one embodiment, the core does not have a core pharmaceutical substance. In another embodiment, the core does have a core pharmaceutical substance.

In one embodiment, the device comprises a core comprising a core polymeric material and multiple layers comprising a layer polymeric material and at least one pharmaceutical substance, where the core polymeric material and the layer polymeric materials may be the same or may be different. In one embodiment, the core does not have a core pharmaceutical substance. In another embodiment, the core does have a core pharmaceutical substance.

In one embodiment, the concentration of pharmaceutical substance in the various layers varies radially in the device. In another embodiment, the concentration varies step-wise with the radius of the device. In another embodiment, the concentration varies linearly with the radius of the device. In another embodiment, the concentration varies both linearly (in some regions) and stepwise (in other regions) of the device. In some embodiments, the concentration of drug in the core is essentially zero percent; in the surrounding layers the concentration of drug decreases with increasing distance from the core, such that the inner-most layer comprises the highest concentration of drug. In one embodiment, the concentration of drug in the core is essentially 0%; in the inner-most surrounding layer, the concentration of drug is about 80%; in the next layer, the concentration of drug is about 60%; in the next layer, the concentration of drug is about 40%; in the outermost layer, the concentration of drug is about 20%.

In one embodiment, the concentration of pharmaceutical substance in the various layers varies radially in the device. In another embodiment, the concentration varies step-wise with the radius of the device. In another embodiment, the concentration varies linearly with the radius of the device. In another embodiment, the concentration varies both linearly (in some regions) and stepwise (in other regions) of the device. In some embodiments, the concentration of drug in the core is essentially zero percent; in the surrounding layers the concentration of drug decreases with decreasing distance from the core, such that the inner-most layer comprises the lowest concentration of drug. In one embodiment, the concentration of drug in the core is essentially 0%; in the inner-most surrounding layer, the concentration of drug is about 20%; in the next layer, the concentration of drug is about 40%; in the next layer, the concentration of drug is about 60%; in the outermost layer, the concentration of drug is about 80%.

In one embodiment, the device comprises a core comprising a core polymeric material. In one embodiment, the device comprises a core comprising essentially 100% polymer. In other embodiments, the core comprises at least about 10%, at least about 20%, at least about 30%, at least about 40%, at least about 50%, at least about 60%, at least about 70%, at least about 75%, at least about 80%, at least about 90%, or at least about 95% polymer, where the remainder of the core comprises a core pharmaceutical substance. In another embodiment, the core is rod-like. In another embodiment the core extends the majority of the length of the device. In another embodiment, the core comprises a lower concentration of drug than the layer or layers surrounding it.

In some embodiments, wherein the implantable device comprises the non-bioerodible polymer EVA, the vinyl acetate content is about 33% by weight. The implantable devices generally comprises about 10% to about 85% pharmaceutical substance or substances, often about 50% to about 75% pharmaceutical substance or substances. In one embodiment, the device comprises about 50% pharmaceutical substance or substances.

In one embodiment, the device comprises a core comprising at least one non-erodible polymer, which is surrounded by one or more layers comprising at least one non-erodible polymer and at least one drug. In another embodiment, the device comprises a core comprising at least one non-erodible polymer, which is surrounded by one or more layers comprising at least one erodible polymer and at least one drug. In another embodiment, the device comprises a core comprising at least one erodible polymer, which is surrounded by one or more layers comprising at least one erodible polymer and at least one drug.

Another embodiment of this invention is a method for delivering a pharmaceutical substance (or substances) to a patient in need thereof, comprising the step of inserting a device subcutaneously into the patient, wherein the pharmaceutical substance (or substances) is released from the device into the patient.

In any of the above embodiments, the first pharmaceutical substance (or first-layer pharmaceutical substance), and any additional pharmaceutical substances (if present), are independently selected from the group consisting of anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, and testosterone.

In one embodiment, the device remains implanted in the patient for at least about 3 months, at least about 6 months, at least about 9 months, at least about 12 months, at least about 15 months, at least about 18 months, at least about 21 months, or at least about 24 months. In one embodiment, the device is removed from the patient after at least about 3 months, at least about 6 months, at least about 9 months, at least about 12 months, at least about 15 months, at least about 18 months, at least about 21 months, or at least about 24 months. In other embodiments, the device remains implanted in the patient indefinitely and does not need to be removed.

In another embodiment, the concentration of pharmaceutical substance in each layer of the device is designed such that an approximately constant or essentially constant amount of pharmaceutical substance is released from the device.

DETAILED DESCRIPTION OF THE INVENTION

Figure 1:
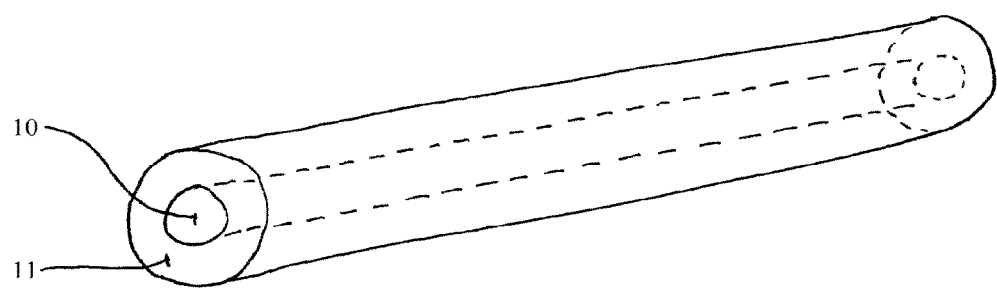
FIG. 1 depicts one embodiment of the invention, encompassing an implantable device for delivery of a pharmaceutical substance to a patient.

The invention provides compositions (i.e., implantable devices), methods, and kits for dosing patients with drug substances. The devices have enhanced mechanical strength which prevent device breakage inside the body. In one embodiment, the device is rod-shaped and contains a rod-shaped inner core comprising a high percentage of polymer for structural integrity. The core is surrounded by one of more layers comprising the same or a different polymer blended with drug. The multiple layers can comprise varying concentrations of drug to shape or maintain the level of drug delivery over time.

Kleppner et al. 2006 J. Pharm. Pharmacol. 58:295-302 describe the breakage of implantable devices inserted into dogs. These devices were inserted into the back of each animal, which is a vulnerable location given dogs' rolling behavior. At 10 months after implant, 70% of the implants were broken. In these devices, the surface area of the two ends equaled approximately 5% of the total surface area. Thus, breaking the device into 2 pieces increased the surface area by 5%; breaking the device into 3 pieces increased the surface area by 10%. Implantation in vulnerable locations in humans would similarly subject the devices to mechanical stress and breakage. This would cause an undesirable increase or potentially uncontrolled change in drug delivery from the device. There is also the potential for injury to the patient from jagged edges which may result from breakage of the implanted device. Finally, breakage of the implant complicates eventual removal of the device. It is believed that the mechanical strength of the implant is decreased over that of the pure polymer due to blending of the polymer with the pharmaceutical substance. Providing an implant with a core having a mechanical strength equal to or close to that of the pure polymer can alleviate problems with implant breakage.

A "core polymeric material" as used herein refers to the polymeric material from which the core of the device is made. A "first-layer polymeric material" as used herein refers to the polymeric material from which the first layer of the device is made. Similarly, "second-layer polymeric material," "third-layer polymeric material," and, generally, "Nth-layer polymeric material" refer to the polymeric material comprising the second layer of the device (if present), the third layer of the device (if present), and, generally, the polymeric material comprising the Nth layer of the device (if present), where N is a positive integer. Blends of two or more polymeric materials can be used for the core polymeric material or any of the layer polymeric materials. The core polymeric material and the layer polymeric materials can be the same polymeric material, different polymeric materials, or some of the core and layer polymeric materials can be the same while others are different.

A "core pharmaceutical substance" as used herein refers to the pharmaceutical substance (if any) contained in the core of the device. A "first-layer pharmaceutical substance" as used herein refers to the pharmaceutical substance contained in the first layer of the device. Similarly, "second-layer pharmaceutical substance," "third-layer pharmaceutical substance," and, generally, "Nth-layer pharmaceutical substance" refer to the pharmaceutical substance in the second layer of the device (if present), the third layer of the device (if present), and, generally, the pharmaceutical substance in the Nth layer of the device (if present), where N is a positive integer. Blends of two or more pharmaceutical substances can be used for the core pharmaceutical substance or any of the layer pharmaceutical substances. The core pharmaceutical substance and the layer pharmaceutical substances can be the same pharmaceutical substance, different pharmaceutical substances, or some of the core and layer pharmaceutical substances can be the same while others are different.

"Drug" and "pharmaceutical substance" are equivalent terms and are used interchangeably.

The invention provides implantable drug delivery devices of heterogeneous composition. Various embodiments of the devices comprise a core comprising polymeric material, where the core is essentially free of drug, or has a sufficiently low concentration of drug such that the mechanical strength of the core remains close to that of the pure polymer. Such a core can provide enhanced mechanical strength, can reduce breakage of the devices after implant, and can improve drug delivery properties of the device.

In one aspect of the invention, the device is generally rod-shaped and comprises a core comprising a core polymeric material, surrounded by one or more layers comprising a first-layer polymeric material, and when more than one layer is present, a second-layer polymeric material through an Nth-layer polymeric material, where N is a positive integer indicating the total number of layers present, and where the first-layer polymeric material and any additional layer polymeric materials may or may not be identical to each other and to the core polymeric material, where the first layer and any additional layers also comprises a pharmaceutical substance or substances. In one aspect, the invention encompasses an implantable device for delivery of a pharmaceutical substance to a patient, comprising a core comprising a core polymeric material and, optionally, a core pharmaceutical substance, surrounded by a first layer comprising a first-layer pharmaceutical substance and a first-layer polymeric material, optionally surrounded by one or more additional layers comprising an additional pharmaceutical substance and an additional polymeric material, where the core, first-layer, and any additional polymeric materials may be the same or different, and where the first and additional pharmaceutical substances may be the same or different.

In one aspect, the device comprises a core comprising a core polymeric material and multiple layers comprising a layer-polymeric material and at least one pharmaceutical substance, where the core polymeric materials and the layer polymeric materials may be the same or different, and where the layer polymeric materials may be the same for all layers, different for all layers, or the same for some layers and different for other layers. The concentration, or average concentration, of pharmaceutical substance in the various layers varies radially in the device. In another embodiment, the concentration varies step-wise with the radius of the device. In another embodiment, the concentration varies linearly with the radius of the device. In another embodiment, the concentration varies both linearly (in some regions) and stepwise (in other regions) of the device. In some embodiments, the concentration of drug in the core is essentially zero percent; in the surrounding layers the concentration of drug decreases with distance from the core, such that the inner-most layer comprises the highest concentration of drug. In one embodiment, the concentration of drug in the core is essentially 0%; in the inner-most surrounding layer, the concentration of drug is about 80%; in the next layer, the drug is 60%; in the next layer, the drug is about 40%; in the outermost layer, the drug is about 20%. In this text, the terminology "concentration" of a drug in a layer or in the core is meant to mean the "average concentration" of the drug in the layer, or in the core, that is referred to; the core or an individual layer may contain the same concentration of drug throughout, or may have a gradient or other non-uniformity of concentration.

Figure 6:
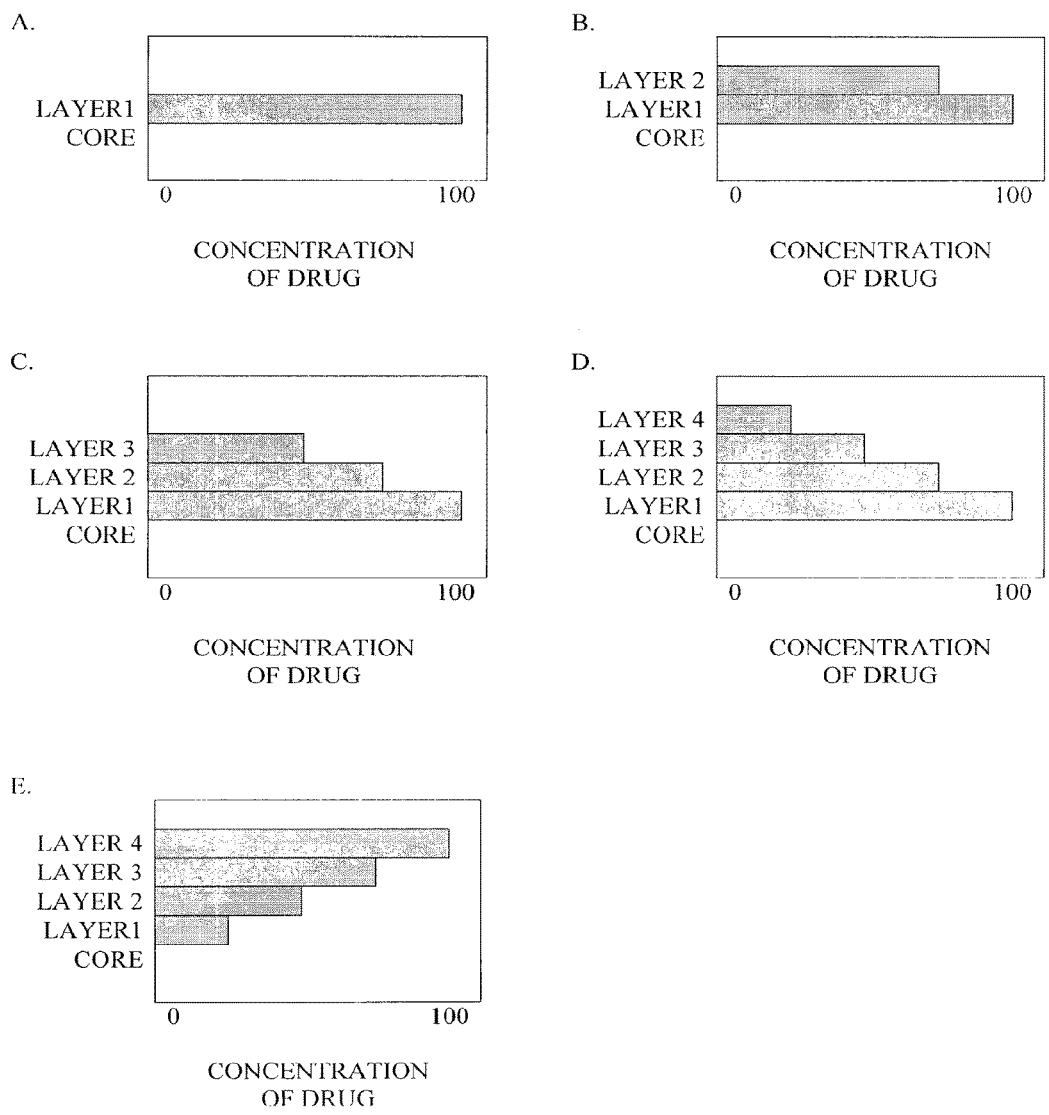
FIG. 6 illustrates variations in drug concentration among layers of some of the embodiments of the invention, indicating how the concentration of pharmaceutical substance in the various layers varies with distance from the core.

The most convenient way of formulating a device where the concentration of pharmaceutical substance (or substances) varies step-wise with the radius of the device is to provide multiple layers with different concentrations of the pharmaceutical substance in each layer. Several such embodiments are illustrated in FIG. 6, where the step-wise nature of the changing concentration of drug corresponds to the concentration of drug in the different layers of the device.

In one aspect, the device comprises a core comprising mostly polymer (the "core polymer") and no or only a small percentage of drug, for example, up to approximately 5%, up to approximately 10%, up to approximately 20%, up to approximately 25%, up to approximately 30%, up to approximately 40%, or up to approximately 50% drug. In one embodiment, the device comprises a core comprising essentially 100% polymer. In other embodiments, the core comprises about or at least about 50% polymer and about or at most about 50% drug, about or at least about 60% polymer and about or at most about 40% drug, about or at least about 70% polymer and about or at most about 30% drug, about or at least about 75% polymer and about or at most about 25% drug, about or at least about 80% polymer and about or at most about 20% drug, about or at least about 85% polymer and about or at most about 15% drug, about or at least about 90% polymer and about or at most about 10% drug, about or at least about 95% polymer and about or at most about 5% drug, about or at least about 96% polymer and about or at most about 4% drug, about or at least about 97% polymer and about or at most about 3% drug, about or at least about 98% polymer and about or at most about 2% drug, or about or at least about 99% polymer and about or at most about 1% drug, or 100% polymer or about 100% polymer. In another embodiment, the core is rod-like or cylindrical. In another embodiment, the core is rod-like or cylindrical, and is rounded at either end, that is, capped by a hemisphere, oblate hemisphere, oblate hemispheroid, or ellipsoid having about the same diameter as the rod-like or cylindrical portion of the core. The portions of the device capping the ends of the rod can be essentially 100% polymer, or can contain the same percentage of polymer and drug as in the core of the device, or can comprises about or at least about 50% polymer and about or at most about 50% drug, about or at least about 60% polymer and about or at most about 40% drug, about or at least about 70% polymer and about or at most about 30% drug, about or at least about 75% polymer and about or at most about 25% drug, about or at least about 80% polymer and about or at most about 20% drug, about or at least about 85% polymer and about or at most about 15% drug, about or at least about 90% polymer and about or at most about 10% drug, about or at least about 95% polymer and about or at most about 5% drug, about or at least about 96% polymer and about or at most about 4% drug, about or at least about 97% polymer and about or at most about 3% drug, about or at least about 98% polymer and about or at most about 2% drug, or about or at least about 99% polymer and about or at most about 1% drug. In another embodiment the core extends the majority of the length of the device. In another embodiment, the core comprises a lower concentration of drug than the layer or layers surrounding it. In another embodiment, the core comprises a higher concentration of drug than the layer or layers surrounding it.

In some aspects, wherein the implantable device comprises EVA, the vinyl acetate content is about 33% by weight. The implantable devices generally comprises about 10% to about 85%, often about 50% to 75% drug. In one embodiment, the device comprises about 50% drug.

In another aspect, the drug substance is blended with the polymer to determine the strength of the polymer-drug mixture. An amount of drug and polymer is blended, a rod the size of the core of the intended device is fabricated, and the breaking point of the rod is measured. Bending or flexure strength is measured; compressive, tensile, shear, and torsion strength can also be measured. International Organization for Standardization or American Society for Testing and Materials (ASTM) standards can be used to test these properties, such as ASTM D790 or ISO 178 (bending/flexure), ASTM D695 or ISO 604 (compressive), ASTM D638 (tensile), and ISO 537 or ISO 6721-2 (shear modulus under torsion). In one embodiment, the polymer/drug substance blend has at least about 20% of the bending, compressive, tensile, shear, or torsional strength of the pure polymer (polymer unblended with drug substance). In another embodiment, the polymer/drug substance blend has at least about 25% of the bending, compressive, tensile, shear, or torsional strength of the pure polymer (polymer unblended with drug substance). In another embodiment, the polymer/drug substance blend has at least about 30% of the bending, compressive, tensile, shear, or torsional strength of the pure polymer (polymer unblended with drug substance). In another embodiment, the polymer/drug substance blend has at least about 40% of the bending, compressive, tensile, shear, or torsional strength of the pure polymer (polymer unblended with drug substance). In another embodiment, the polymer/drug substance blend has at least about 50% of the bending, compressive, tensile, shear, or torsional strength of the pure polymer (polymer unblended with drug substance). In another embodiment, the polymer/drug substance blend has at least about 60% of the bending, compressive, tensile, shear, or torsional strength of the pure polymer (polymer unblended with drug substance). In another embodiment, the polymer/drug substance blend has at least about 70% of the bending, compressive, tensile, shear, or torsional strength of the pure polymer (polymer unblended with drug substance). In another embodiment, the polymer/drug substance blend has at least about 75% of the bending, compressive, tensile, shear, or torsional strength of the pure polymer (polymer unblended with drug substance). In another embodiment, the polymer/drug substance blend has at least about 80% of the bending, compressive, tensile, shear, or torsional strength of the pure polymer (polymer unblended with drug substance). In another embodiment, the polymer/drug substance blend has at least about 90% of the bending, compressive, tensile, shear, or torsional strength of the pure polymer (polymer unblended with drug substance). In the aforementioned embodiments, a preferred measure of strength is bending (flexure) strength.

In one aspect, the device comprises a core comprising at least one non-erodible polymer, which is surrounded by one or more layers comprising at least one non-erodible polymer and at least one drug. In another embodiment, the device comprises a core comprising at least one non-erodible polymer, which is surrounded by one or more layers comprising at least one erodible polymer and at least one drug. In another embodiment, the device comprises a core comprising at least one erodible polymer, which is surrounded by one or more layers comprising at least one erodible polymer and at least one drug.

Another aspect of this invention is a method for delivering a pharmaceutical substance to a patient in need thereof, comprising the step of inserting a device subcutaneously into the patient, wherein the pharmaceutical substance is released from the device into the patient.

In one aspect, the device remains implanted in the patient for at least about 3 months, at least about 6 months, at least about 9 months, at least about 12 months, at least about 15 months, at least about 18 months, at least about 21 months, or at least about 24 months.

In another aspect, the concentration of pharmaceutical substance in each layer of the device is designed such that a steady-state level or approximately constant level or essentially constant level of pharmaceutical substance is released into the patient. In another aspect, the devices provide a steady-state level or approximately constant level or essentially constant level of pharmaceutical substance in the plasma of the patient.

In one embodiment, the invention comprises a rod-shaped core comprising a polymer with essentially no pharmaceutical substance. This core is surrounded by a single layer comprising a polymer and a pharmaceutical substance. In one embodiment of this type, the rod is about 2 to about 3 cm in length, e.g., about 2.6 cm, and about 2 mm to about 3 mm in diameter; the single layer is about 0.5 mm to about 1 mm in thickness, and the core is about 0.5 mm to about 2 mm in diameter. In one embodiment, both the core and the single layer comprise the same polymer, for example, ethylene vinyl acetate (EVA). In another embodiment, the core comprises a polymer, for example, ethylene vinyl acetate (EVA); the layer comprises a different polymer, e.g., a bioerodible polymer such as PLGA. The single layer comprises about 10% to about 90% of a pharmaceutical substance, for example, anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. In one embodiment, the pharmaceutical substance is buprenorphine.

In one embodiment, the invention comprises a rod-shaped core comprising a polymer with essentially no pharmaceutical substance. This core is surrounded by two layers comprising a polymer and a pharmaceutical substance. In one embodiment of this type, the rod is about 2 to about 3 cm in length, e.g., about 2.6 cm, and about 2 mm to about 5 mm in diameter; each layer is about 0.5 to about 1 mm in thickness, and the core is about 0.5 mm to about 2 mm in diameter. In one embodiment, the core and both layers all comprise the same polymer, for example, ethylene vinyl acetate (EVA). In another embodiment, the core comprises a polymer, for example, ethylene vinyl acetate (EVA); the layers comprise a different polymer, e.g., a bioerodible polymer such as PLGA. Both layers comprise a pharmaceutical substance, which may be the same substance in each layer or different substances in each layer, for example, a substance independently selected from anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. The layers can independently comprise about 10% to about 90% of the pharmaceutical substance(s). In one embodiment, both layers contain the same pharmaceutical substance, and the outermost layer comprises a lower concentration of the pharmaceutical substance than the innermost layer; e.g., the outermost layer comprises about 10% to about 90% of a pharmaceutical substance and the innermost layer comprises about 10% to about 90% of the pharmaceutical substance, where the outermost layer comprises a lower concentration of the pharmaceutical substance than the innermost layer. In one such embodiment, the pharmaceutical substance in both layers is buprenorphine.

In one embodiment, the invention comprises a rod-shaped core comprising a polymer with essentially no pharmaceutical substance. The core is surrounded by three layers comprising a polymer and a pharmaceutical substance. In one embodiment of this type, the rod is about 2 to about 3 cm in length, e.g., about 2.6 cm, and about 3 mm to about 7 mm in diameter; each layer is about 0.5 mm to about 1 mm in thickness, and the core is about 0.5 to about 2 mm in diameter. In one embodiment, the core and all the layers all comprise the same polymer, for example, ethylene vinyl acetate (EVA). In another embodiment, the core comprises a polymer, for example, ethylene vinyl acetate (EVA); the layers comprise a different polymer, e.g., a bioerodible polymer such as PLGA. All the layers comprise a pharmaceutical substance which may be the same substance in each layer, different substances in each layer, or the same in two of the layers and different in the third layer, for example, a substance independently selected from anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. The layers can independently comprise about 10% to about 90% of the pharmaceutical substance(s). In one embodiment, each layer contains the same pharmaceutical substance, but the layers differ in the concentration of the pharmaceutical substance, such that the average concentration of the pharmaceutical substance in each layer decreases with increasing distance from the core. Thus the outermost layer comprises about 10% to about 90% of the pharmaceutical substance, while the middle layer comprises about 10% to about 90% of the pharmaceutical substance, and the innermost layer comprises about 10% to about 90% of the pharmaceutical substance, subject to the condition that the outer layer has a lower concentration of pharmaceutical substance than the middle layer, while the inner layer (adjacent to the core) has a higher concentration of pharmaceutical substance than the middle layer. In one such embodiment, the pharmaceutical substance in all three layers is buprenorphine.

In one embodiment, the invention comprises a rod-shaped core comprising a polymer with essentially no pharmaceutical substance. The core is surrounded by four layers comprising a polymer and a pharmaceutical substance. In one embodiment of this type, the rod is about 2 cm to about 3 cm in length, e.g., about 2.6 cm, and about 4 mm to about 9 mm in diameter; each layer is about 0.5 mm to about 1 mm in thickness, and the core is about 0.5 mm to about 1 mm in thickness. In one embodiment, the core and all the layers all comprise the same polymer, for example, ethylene vinyl acetate (EVA). In another embodiment, the core comprises a polymer, for example, ethylene vinyl acetate (EVA); the layers comprise a different polymer, e.g., a bioerodible polymer such as PLGA. All the layers comprise a pharmaceutical substance, for example, a substance independently selected from anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. The layers can independently comprise about 10% to about 90% of the pharmaceutical substance(s). In one embodiment, each layer contains the same pharmaceutical substance, but the layers differ in the concentration of the pharmaceutical substance, such that the average concentration of the pharmaceutical substance in each layer decreases with increasing distance from the core. Thus the outermost layer comprises about 10% to about 90% of the pharmaceutical substance, the second-outermost layer comprises about 10% to about 90% of the pharmaceutical substance, the third-outermost layer comprises about 10% to about 90%, of the pharmaceutical substance and the innermost layer (adjacent to the core) comprises about 10% to about 90% of the pharmaceutical substance, subject to the condition that the outermost layer has a concentration of the pharmaceutical substance lower than the concentration in the second-outermost layer, the second-outermost layer has a concentration of the pharmaceutical substance lower than the concentration in the third-outermost layer, and the third-outermost layer has a concentration of the pharmaceutical substance lower than the innermost layer (adjacent to the core). In one such embodiment, the pharmaceutical substance in all four layers is buprenorphine.

In one embodiment, the invention comprises a rod-shaped core comprising a polymer with essentially no pharmaceutical substance. The core is surrounded by five layers comprising a polymer and a pharmaceutical substance. In one embodiment of this type, the rod is about 2 cm to about 3 cm in length, e.g., about 2.6 cm, and about 5 mm to about 10 mm in diameter; each layer is about 0.5 mm to about 1 mm in thickness, and the core is about 0.5 mm to about 1 mm in thickness. In one embodiment, the core and all the layers all comprise the same polymer, for example, ethylene vinyl acetate (EVA). In another embodiment, the core comprises a polymer, for example, ethylene vinyl acetate (EVA); the layers comprise a different polymer, e.g., a bioerodible polymer such as PLGA. All the layers comprise a pharmaceutical substance, for example, a substance independently selected from anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. The layers can independently comprise about 10% to about 90% of the pharmaceutical substance(s). In one embodiment, each layer contains the same pharmaceutical substance, but the layers differ in the concentration of the pharmaceutical substance, such that the average concentration of the pharmaceutical substance in each layer decreases with increasing distance from the core. Thus the outermost layer comprises about 10% to about 90% of the pharmaceutical substance, the second-outermost layer comprises about 10% to about 90% of the pharmaceutical substance, the third-outermost layer comprises about 10% to about 90%, of the pharmaceutical substance and the innermost layer (adjacent to the core) comprises about 10% to about 90% of the pharmaceutical substance, subject to the condition that the outermost layer has a concentration of the pharmaceutical substance lower than the concentration in the second-outermost layer, the second-outermost layer has a concentration of the pharmaceutical substance lower than the concentration in the third-outermost layer, the third-outermost layer has a concentration of the pharmaceutical substance lower than the fourth-outermost layer, and the fourth-outermost layer has a concentration of the pharmaceutical substance lower than the innermost layer (adjacent to the core). In one such embodiment, the pharmaceutical substance in all five layers is buprenorphine.

In additional embodiments, the invention can comprise additional layers, each layer having a decreasing concentration of pharmaceutical substance as the distance from the core increases, in a manner similar to that described above.

In any of the above embodiments, one or more of the layers can be non-bioerodible. In any of the above embodiments, all of the layers can be non-bioerodible. In any of the above embodiments, the core can be non-bioerodible. In any of the above embodiments, the core and one or more of the layers can be non-bioerodible, with the proviso that no non-bioerodible material is external to a bioerodible layer or a bioerodible core (i.e., if the device has any bioerodible layers, then any additional layers which are external to that layer must be bioerodible; equivalently, if the device has any non-bioerodible layers, then any bioerodible layers are located external to that layer, that is, the bioerodible layers are farther from the core than any non-bioerodible layers. This condition also requires all layers to be bioerodible if the core is bioerodible). In any of the above embodiments, the core and all of the layers can be non-bioerodible.

In any of the above embodiments, one or more of the layers can be bioerodible. In any of the above embodiments, all of the layers can be bioerodible, while the core is non-bioerodible. In any of the above embodiments, the core and each of the one or more layers are bioerodible.

In any of the above embodiments, one or more of the layers can comprise a mixture of a bioerodible polymer and a non-bioerodible polymer. The mixture can be blended together prior to extruding in the same layer. Alternatively, the mixture can be co-extruded into the same layer at the time of forming the layer. In various embodiments, the proportion of bioerodible polymer to non-erodible polymer in the mixed layer can be about 10% bioerodible and 90% non-erodible, about 20% bioerodible and 80% non-erodible, about 25% bioerodible and 75% non-erodible, about 30% bioerodible and 70% non-erodible, about 33% bioerodible and 67% non-erodible, about 40% bioerodible and 60% non-erodible, about 50% bioerodible and 50% non-erodible, about 60% bioerodible and 40% non-erodible, about 67% bioerodible and 33% non-erodible, about 70% bioerodible and 30% non-erodible, about 75% bioerodible and 25% non-erodible, about 80% bioerodible and 20% non-erodible, or about 90% bioerodible and 10% non-erodible. In one embodiment, the bioerodible polymer is chosen from any of the bioerodible polymers recited elsewhere in this specification. In one embodiment, the non-erodible polymer is chosen from any of the non-erodible polymers recited elsewhere in this specification. In any of the foregoing embodiments of mixed layers, the bioerodible polymer can be PLGA. In any of the foregoing embodiments of mixed layers, the non-erodible polymer can be EVA. In any of the foregoing embodiments of mixed layers, the bioerodible polymer can be PLGA and the non-erodible polymer can be EVA. When a layer is used which comprises a mixture of a bioerodible polymer and a non-bioerodible polymer, any layers external to that mixed layer are either bioerodible or mixed bioerodible/non-erodible.

In one embodiment, the invention comprises a rod-shaped core comprising a polymer with essentially no pharmaceutical substance. This core is surrounded by two layers comprising a polymer and a pharmaceutical substance. In one embodiment of this type, the rod is about 2 cm to about 3 cm in length, e.g., about 2.6 cm, and about 2 mm to about 5 mm in diameter; each layer is about 0.5 mm to about 1 mm in thickness, and the core is about 0.5 mm to 2 mm in diameter. In one embodiment, the core and all the layers all comprise the same polymer, for example, ethylene vinyl acetate (EVA). In another embodiment, the core comprises a polymer, for example, ethylene vinyl acetate (EVA); the layers comprises a different polymer, e.g., a bioerodible polymer such as PLGA, and each layer comprises the same bioerodible polymer. Both layers comprise a pharmaceutical substance, for example, a substance independently selected from anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. In one embodiment, both layers contain the same pharmaceutical substance, and the outermost layer comprises a higher concentration of the pharmaceutical substance than the innermost layer; e.g., the outermost layer comprises about 10% to about 90% of a pharmaceutical substance and the innermost layer comprises about 10% to about 90% of the pharmaceutical substance, where the outermost layer comprises a higher concentration of the pharmaceutical substance than the innermost layer. In one such embodiment, the pharmaceutical substance in both layers is buprenorphine. Optionally, this embodiment can comprise additional layers comprising polymer and pharmaceutical substance; in this case, the outermost layer comprises the highest concentration of pharmaceutical substance, with each more inner layer comprising a lower level of drug. This is illustrated in FIG. 6E. This configuration allows an initial high rate of drug release into the patient over a certain period, and thus a higher initial serum or systemic level of drug, followed by a decreasing release rate over time which results in a lower subsequent serum or systemic level of drug, which gradually decreases over a period of time. In another embodiment, wherein the outermost layer also comprises the highest concentration of drug, the inner-more layers can comprise approximately equal concentrations of drug, yet all lower than the outermost layer. This will allow an initial high rate of drug release into the patient over a certain period, and thus a higher initial serum or systemic level of drug, followed by a lower, essentially steady-state level of drug over a period of time.

In additional embodiments, the invention can comprise additional layers, each layer having an increasing concentration of pharmaceutical substance as the distance from the core increases.

In one embodiment, the invention comprises a rod-shaped core comprising a polymer with essentially no pharmaceutical substance. This core is surrounded by a single layer comprising a polymer and a pharmaceutical substance. Finally, the single layer is surrounded by a layer of essentially pure pharmaceutical substance. In one embodiment of this type, the rod is about 2 to about 3 cm in length, e.g., about 2.6 cm, and about 2 mm to about 3 mm in diameter; the single layer is about 0.5 mm to about 1 mm in thickness, and the core is about 0.5 mm to about 2 mm in diameter, while the thickness of the layer of pure drug is determined by the amount of pure drug to be used. In one embodiment, both the core and the single layer comprise the same polymer, for example, ethylene vinyl acetate (EVA). In another embodiment, the core comprises a polymer, for example, ethylene vinyl acetate (EVA); the layer comprises a different polymer, e.g., a bioerodible polymer such as PLGA. The single layer comprises about 10% to about 90% of a pharmaceutical substance, for example, anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. The layer of pure drug comprises about 100% of a pharmaceutical substance, independently selected from, for example, anastrozole, apomorphine, beraprost, buprenorphine, buserelin, dutasteride, finasteride, haloperidol, iloprost, L-thyroxine, L-triiodothryonine, leuprolide, lisuride, nalmefene, nicotine, pramipexole, rasagiline, risperidone, ropinerole, rotigotine, selegiline, sirolimus, tacrolimus, tamsulosin, or testosterone. In one embodiment, the pharmaceutical substance in both the single layer and the layer of pure drug is buprenorphine.

In additional embodiments, the invention can comprise additional layers, each layer having an increasing concentration of pharmaceutical substance as the distance from the core increases, with a layer of essentially pure pharmaceutical substance on the outside of the device. This configuration allows an initial high rate of drug release into the patient over a certain period, and thus a higher initial serum or systemic level of drug.

In one aspect, the invention provides an implantable device for delivering a pharmaceutical substance, comprising the substance and a biocompatible polymeric matrix. The drug is encapsulated within the matrix, and the implantable device is subcutaneously implanted in a mammal such as a dog or cat or human being. The pharmaceutical substance is continuously released from the device over a sustained period of time through pores that open in the surface of the matrix. The drug is delivered, for example, at a rate of at least about 0.1 mg per day, generally in the range of about 0.1 to about 5 mg per day. In some embodiments, the steady state rate of drug release is about 0.3 mg per day. The rate of drug release, which is determined by the size and other physical parameters of the device, implant location, and concentration of drug in various layers of the implant, can be tailored to provide a desired dosage in relation to a patient's ailment, physical condition and weight or body surface area.

Various non-limiting embodiments of the invention are depicted in FIGS. 1 to 6. FIG. 1 depicts one embodiment of the invention, encompassing an implantable device for delivery of a pharmaceutical substance to a patient, comprising: a core 10 comprising a core polymeric material; and a first layer 11 comprising a first-layer pharmaceutical substance and a first-layer polymeric material surrounding the core, where the core polymeric material and the first-layer polymeric material are the same or different. The core and the first layer may thus comprise the same or different polymeric materials. If the core contains pharmaceutical substance, the core and the first layer may comprise the same pharmaceutical substance or different pharmaceutical substances.

Figure 2:
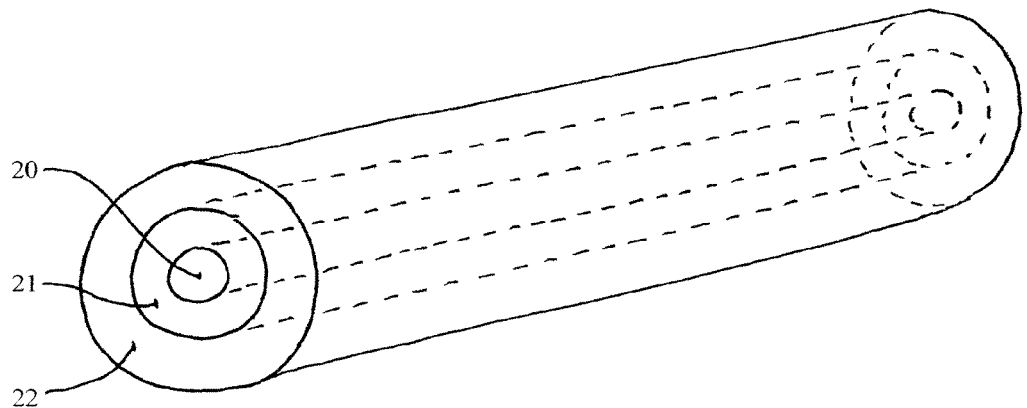
FIG. 2 depicts another embodiment of the invention, encompassing an implantable device for delivery of a pharmaceutical substance to a patient.

FIG. 2 depicts another embodiment of the invention, encompassing an implantable device for delivery of a pharmaceutical substance to a patient, comprising: a core 20 comprising a core polymeric material; and a first layer 21 comprising a first-layer pharmaceutical substance and a first-layer polymeric material surrounding the core; and a second layer 22 comprising a second-layer pharmaceutical substance and a second-layer polymeric material, where the core, first-layer, and second-layer polymeric materials are the same or different, and where the first-layer and second-layer pharmaceutical substances are the same or different. The core and each layer may thus comprise the same or different polymeric materials. Each layer may comprise the same pharmaceutical substance or different pharmaceutical substances. If the core contains pharmaceutical substance, the core and each layer may comprise the same pharmaceutical substance or different pharmaceutical substances.

Figure 3:
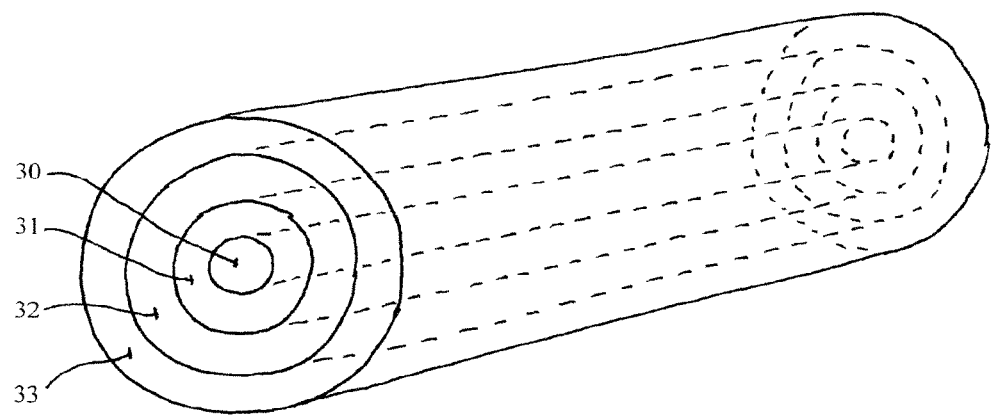
FIG. 3 depicts another embodiment of the invention, encompassing an implantable device for delivery of a pharmaceutical substance to a patient.

FIG. 3 depicts another embodiment of the invention, encompassing an implantable device for delivery of a pharmaceutical substance to a patient, comprising: a core 30 comprising a core polymeric material; and a first layer 31 comprising a first-layer pharmaceutical substance and a first-layer polymeric material surrounding the core; and a second layer 32 comprising a second-layer pharmaceutical substance and a second-layer polymeric material, and an additional layer 33 comprising a third-layer pharmaceutical substance and a third-layer polymeric material, where the core, first-layer, second-layer and third-layer polymeric materials are the same or different, and where the first-layer, second-layer and third-layer pharmaceutical substances are the same or different. The core and each layer may thus comprise the same or different polymeric materials. Each layer may comprise the same pharmaceutical substance or different pharmaceutical substances. If the core contains pharmaceutical substance, the core and each layer may comprise the same pharmaceutical substance or different pharmaceutical substances.

Figure 4:
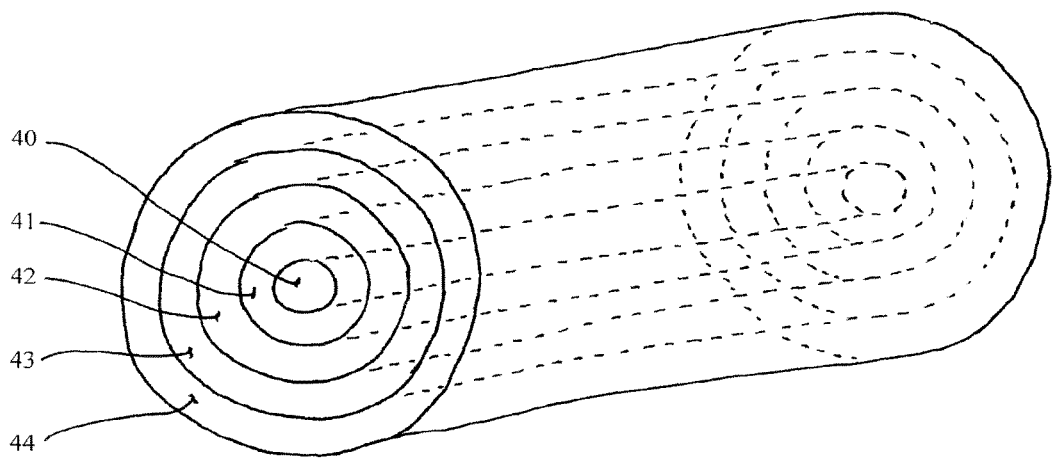
FIG. 4 depicts another embodiment of the invention, encompassing an implantable device for delivery of a pharmaceutical substance to a patient.

FIG. 4 depicts another embodiment of the invention, encompassing an implantable device for delivery of a pharmaceutical substance to a patient, comprising: a core 40 comprising a core polymeric material; and a first layer 41 comprising a first-layer pharmaceutical substance and a first-layer polymeric material surrounding the core; and a second layer 42 comprising a second-layer pharmaceutical substance and a second-layer polymeric material, a third layer 43 comprising a third-layer pharmaceutical substance and a third-layer polymeric material, and a fourth layer 44 comprising a fourth-layer pharmaceutical substance and a fourth-layer polymeric material, where the core, first-layer, second-layer, third-layer, and fourth-layer polymeric materials are the same or different, and where the first-layer, second-layer, third-layer, and fourth-layer pharmaceutical substances are the same or different. The core and each layer may thus comprise the same or different polymeric materials. Each layer may comprise the same pharmaceutical substance or different pharmaceutical substances. If the core contains pharmaceutical substance, the core and each layer may comprise the same pharmaceutical substance or different pharmaceutical substances.

Figure 5:
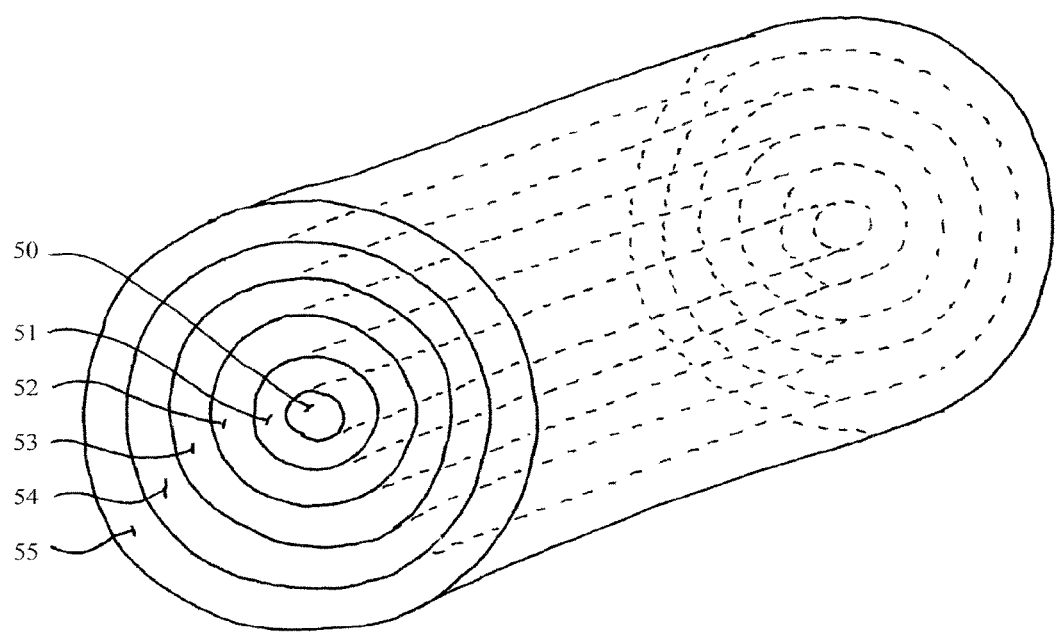
FIG. 5 depicts another embodiment of the invention, encompassing an implantable device for delivery of a pharmaceutical substance to a patient.

FIG. 5 depicts another embodiment of the invention, encompassing an implantable device for delivery of a pharmaceutical substance to a patient, comprising: a core 50 comprising a core polymeric material; and a first layer 51 comprising a first-layer pharmaceutical substance and a first-layer polymeric material surrounding the core; and a second layer 52 comprising an second-layer pharmaceutical substance and a second-layer polymeric material, a third layer 53 comprising a third-layer pharmaceutical substance and a third-layer polymeric material, a fourth layer 54 comprising a fourth-layer pharmaceutical substance and a fourth-layer polymeric material, and a fifth layer 55 comprising a fifth-layer pharmaceutical substance and fifth-layer polymeric material, where the core, first, second, third, fourth, and fifth polymeric materials are the same or different, and where the first, second, third, fourth, and fifth pharmaceutical substances are the same or different. The core and each layer may thus comprise the same or different polymeric materials. Each layer may comprise the same pharmaceutical substance or different pharmaceutical substances. If the core contains pharmaceutical substance, the core and each layer may comprise the same pharmaceutical substance or different pharmaceutical substances.

FIG. 6 diagrams several embodiments of the invention, in which the concentration of pharmaceutical substance in the various layers varies with varying distance from the core. In the embodiment depicted in FIG. 6A, the invention comprises a core comprising essentially no drug, with one layer (Layer 1) comprising a high percentage of drug (approximately 80 to approximately 90%). In the embodiment depicted in FIG. 6B, the invention comprises a core comprising essentially no drug, with one layer (Layer 1) comprising a high percentage of drug (approximately 80 to approximately 90%), surrounded by an outermost layer (Layer 2) comprising a lower concentration of drug than Layer 1 (approximately 60 to 70%). In the embodiment depicted in FIG. 6C, the invention comprises a core comprising essentially no drug, with one layer (Layer 1) comprising a higher percentage of drug (approximately 80 to approximately 90%), surrounded by another layer (Layer 2) comprising a lower concentration of drug than Layer 1 (approximately 60 to approximately 70%), surrounded by an outermost layer (Layer 3), comprising a concentration of drug lower than Layer 2 (approximately 50%). In the embodiment depicted in FIG. 6D, the invention comprises a core comprising essentially no drug, surrounded by a layer (Layer 1) comprising a higher percentage of drug (approximately 80 to approximately 90%), surrounded by another layer (Layer 2), comprising a concentration of drug lower than Layer 1 (approximately 60 to approximately 70%), surrounded by another layer (Layer 3), comprising a concentration of drug lower than Layer 2 (approximately 50%), surrounded by an outermost layer (Layer 4) comprising a concentration of drug lower than Layer 3 (approximately 30 to approximately 40%). In the embodiment depicted in FIG. 6E, the invention comprises a core comprising essentially no drug, surrounded by a layer (Layer 1) comprising a low level of drug (approximately 30 to approximately 40%), surrounded by a layer (Layer 2) comprising a higher level of drug (approximately 50%), surrounded by a layer (Layer 3) comprising a still higher level of drug (approximately 60 to approximately 70%), surrounded by an outermost layer (Layer 4) comprising a still higher percentage of drug (approximately 80 to approximately 90%). In this last embodiment, each successive layer comprises an increasing percentage of pharmaceutical substance with increasing distance from the core, with the highest percentage of drug in the outermost layer.

Manufacture of the Devices

In some embodiments, the implantable devices can be produced by an extrusion process. The drug substance can be prepared by milling (e.g., ball-milling, impact-milling), spray-drying, solvent precipitation, screening or other method or combination of methods known in the art to produce fine particles. The drug can be combined with a polymer which is also prepared as fine particles. The blended mixture can be extruded, e.g., via Microtruder screw extruder, Model No. RCP-025, Randcastle Extrusion Systems, Cedar Grove, N.J., or via other extrusion devices known in the industry. The diameter of extrusion, as well as temperature, pressure and other parameters can be controlled as appropriate for each drug.

In another embodiment, a core comprising polymer can be formed, e.g., by extrusion, which is then coated with one or more layers comprising polymer and drug via a dip coating or spray coating method. A solvent evaporation technique may be used to mix the polymer and drug in a solvent. The solution comprising polymer, drug and solvent can then be applied to the surface of the core by either dipping or spraying. The resultant composition is then subjected to a drying process, during which the solvent is evaporated, and the polymeric material, with the drug dispersed therein, forms a thin film or layer on the core. This procedure can be repeated with various solutions of the same or differing concentrations of drug and polymer to deposit additional layers on the composition. As is known in the art, devices comprising multiple layers may be produced by any combination of extrusion and coating.

The extrudate can be extruded horizontally and collected for further processing. The extrudate can be cut into desirable lengths, e.g., from about 1 to about 3 cm. The extrudate can then be washed in any solvent in which the drug or drugs dissolve, and then dried and packaged.

Devices with multiple layers can be produced by co-extrusion methods known in the art, for example, by the methods disclosed in U.S. Pat. No. 5,063,018 (for manufacturing catheters with a lumen), or U.S. Pat. Nos. 4,832,589, 4,379,117, 3,880,691, and 3,337,665. Multi-manifold dies, such as multi-manifold dies using feedblock co-extrusion, are known in the art for producing multi-layered materials.

Physical Parameters of the Devices

In some embodiments, devices comprise dimensions of about 0.5 to about 7 mm in diameter. In some embodiments the devices are about 0.5 to 10 cm in length. In one embodiment, the device is from about 1 to about 3 cm in length. In one embodiment, the device is about 2 cm to about 3 cm in length. In another embodiment, the device is about 2.6 cm in length. In one embodiment, the device is about 1 to about 3 mm in diameter. In another embodiment, the device is about 2 to about 3 mm in diameter. In one embodiment, the device is about 2.4 mm in diameter. In some embodiments in which devices comprises dimensions of about 2.4 mm in total diameter and about 2.6 cm in total length, the devices each release 1 mg of pharmaceutical substance per day.

In some embodiments, the core comprising a polymeric material and the layer or layers comprising a polymeric material and a drug are each independently about 0.5 to about 7 mm in diameter or thickness. In one embodiment, the core and layer or layers are each independently about 0.5 to about 3.5 mm. In another embodiment, the core and layer or layers are each independently about 0.5 to about 2 mm. In another embodiment, the core and layer or layers are each independently about 1 to about 2 mm. The thickness or diameter of the core may vary from the thickness of the layer or layers. If multiple layers are present, each layer may have the same thickness as the other layers, or each layer may have a different thickness from the other layers, or some layers may have the same thickness as other layers while some layers may have a different thickness from other layers. By "thickness" of a layer is meant the distance, as measured from the center of the device, between the start of the layer and the end of the layer; for example, for a cylindrical device with regular, annular layers, a layer that starts at 2 mm from the center and that ends at 3.5 mm from the center has a thickness of 1.5 mm.

Although the device may be illustrated as having a core and one or more layers which are cylindrical or annular in cross-section, it is understood that the cross-section of the core and one or more layers may be oval, polygonal, star-shaped, irregular, or of uneven thickness.

In some embodiments, the various layers comprising a polymer and drug may comprise different polymers, or mixtures thereof, and different drugs or mixtures thereof.

Drug Release

The release of drug from the device is dependent on the rate of dissolution and on passive diffusion through the polymer matrix. Therefore, the surface area of the implant determines the rate of release. The release mechanism of the drug from the polymeric material also depends on the nature of the polymer and the drug. The drug diffuses through the polymer to the surrounding tissues and bodily fluids. Release can also occur through degradation or erosion of the polymer, in the case of an erodible or bioerodible polymer. The degradation or erosion of the polymer may occur through hydrolysis, by enzymatic degradation, or via other processes.

Drug release rates are also affected by washing of the implant prior to insertion into the patient. Washed implants maintain a more-stable release rate after insertion; unwashed implants may show a significantly higher burst release immediately after implant. A burst release may be detrimental to the patient, as local or systemic drug concentration rises from zero to a potentially supra-therapeutic level rapidly. Initial burst may also unnecessarily deplete the drug depot and shorten the duration of the release period. The implants may be washed with any solvent in which the drug dissolves, such as water, ethanol, isopropanol, etc. Washing may be followed by drying to remove the solvent. Drying may be followed by packaging and sterilization.

In some circumstances, an initial high dose of a drug is desirable, and in those circumstances washing of the device can be omitted in order to provide for an initial burst as a loading dose. In certain embodiments of the device, a layer of substantially pure pharmaceutical substance is placed on the outside of the device, for an enhanced loading dose (initial dose).

In a non-limiting example, the extruded device can be cut into implants of appropriate length, such as 2.6 cm. The extrudate may be, optionally, washed, e.g., with 95% ethanol at room temperature for 30 min to remove surface drug. The washed implants can be dried (e.g., air dried at room temperature for 30 min, then forced air at 40° C. for 1 hour, followed by vacuum drying at 30° C. for 24 hours) to remove residual ethanol. Implants may be placed in moisture barrier foil pouches, heat-sealed and then sterilized using gamma irradiation (2.9-3.1 Mrads).

"Steady state plasma level" refers to an approximately constant level of drug over a period of time in the plasma of the subject or patient. In one embodiment, a steady state plasma level or approximately constant level of drug varies by no more than about ±30% over a day, over a week, over a month, over three months, over six months, or over nine months, as compared to the mean or average plasma level over that time period. In another embodiment, a steady state plasma level or approximately constant level of drug varies by no more than about ±20% over a day, over a week, over a month, over three months, over six months, or over nine months, as compared to the mean or average plasma level over that time period. In another embodiment, a steady state plasma level or approximately constant level of drug varies by no more than about ±10% over a day, over a week, over a month, over three months, over six months, or over nine months, as compared to the mean or average plasma level over that time period. An "approximately constant release rate" indicates that an approximately constant level of the pharmaceutical substance is released from the device over a period of time, such as over a day, over a week, over a month, over three months, over six months, or over nine months. In some embodiments, the approximately constant release rate is no more than about ±30%, ±20%, or ±10% over the time period indicated, as compared to the average or mean release. An approximately constant release rate is preferred in order to achieve a steady state plasma level.

By "essentially constant" is meant that for about 95% of the extended period of time, the concentration of drug in blood plasma is within about three, about two, or preferably about one standard deviation of the mean blood plasma level. Measurements of the blood plasma level can be performed hourly, twice a day, daily, twice a week, weekly, every two weeks, monthly, or at any other periodic interval for determination of the mean plasma levels. For example, if the mean blood plasma level of a drug sampled at weekly intervals is 2.0 ng/ml, and one standard deviation of the measurement is ±0.1 ng/ml, then blood levels that fall within about ±0.3 ng/ml, about ±0.2 ng/ml, or preferably about ±0.1 ng/ml for about 95% of the measurements are considered essentially constant. By "extended periods of time" is meant from about 3 months to about 1 year, or longer, e.g., at least about 3, about 6, about 9, about 12, about 15, about 18, about 21, or about 24 months or more.

In embodiments where an initial burst or an initial loading dose is desired (such as embodiments where excess pharmaceutical substance is not washed off of the surface of the implant, or embodiments where the implant is surrounded by a layer of pure drug), the period during which the initial burst or initial loading dose occurs is excluded from the calculation of steady-state plasma levels or steady-state release rates, approximately constant plasma levels or approximately constant release rates, or essentially constant plasma levels or essentially constant release rates. The initial burst period or initial loading dose period ends when the release rate or plasma level falls within the ranges as specified above for steady-state, approximately constant, or essentially constant.

Exemplary Polymers

The implantable device comprises a core comprising a core polymeric material (optionally also containing pharmaceutical substance), surrounded by one or more layers comprising a layer polymeric material and a pharmaceutical substance. The core and layer polymeric materials may be the same or different. The core or any layer may also comprise a mixture of two or more polymers; the core and the various layers may contain different mixtures of polymers. The polymer can be bioerodible or non-bioerodible. Thus, the core may comprise a bioerodible polymer, and the one or more surrounding layers also comprise bioerodible polymers. In another embodiment, the core may comprise a non-bioerodible polymer, while one or more surrounding layers may comprise a bioerodible polymer or polymers. In another embodiment, both the core and at least one surrounding layer may comprise non-bioerodible polymers. Adjoining layers surrounding the core may comprise bioerodible and non-bioerodible polymers, with the proviso that any bioerodible polymer layers are located outside any non-bioerodible polymer layers, that is, any bioerodible polymer layers are located farther from the core than any non-erodible polymer layers.

As used herein, a "polymer" or "polymeric material" means a macromolecule comprising repeating monomer units or co-monomer units. The polymer may be bioerodible or non-bioerodible. The polymer may be a homopolymer, copolymer, terpolymer, or may contain more than three monomers. The polymer is preferably biocompatible.

Exemplary polymers that can be used for making the device include: acrylics, agarose, alginate, and combinations, cellulose ethers, collagen, copolymers containing poly (ethylene glycol) and polybutylene terephthalate segments (PEG/PBT) (PolyActive™), copolymers of poly(lactic) and glycolic acid, copolymers thereof with poly(ethylene glycol), derivatives and mixtures thereof, dextran, dextrose, elastin, epoxides, ethylene vinyl acetate (EVA copolymer), fluoropolymers, gelatin, hydroxypropylmethylcellulose, maleic anhydride copolymers, methyl cellulose and ethyl cellulose, non-water soluble cellulose acetate, non-water soluble chitosan, non-water soluble hydroxyethyl cellulose, non-water soluble hydroxypropyl cellulose, peptides, PLLA-poly-glycolic acid (PGA) copolymer (also known as poly-L-lactic acid-co-glycolic acid, or PLGA), poly (L-lactic acid), poly(2-ethoxyethyl methacrylate), poly(2-hydroxyethyl methacrylate), poly(2-methoxyethyl acrylate), poly(2-methoxyethyl methacrylate), poly(acrylamide), poly (alginic acid), poly(amino acids), poly(anhydrides), poly (aspartic acid), poly(benzyl glutamate), poly(beta-hydroxybutyrate), poly(caprolactone), poly(D,L-lactic acid), poly(D, L-lactide)(PLA), poly(D,L-lactide-co-caprolactone)(PLA/PCL) and poly(glycolide-co-caprolactone) (PGA/PCL), poly(D,L-lactide-co-glycolide) (PLA/PGA), poly(etherurethane urea), poly(ethyl glutamate-co-glutamic acid), poly (ethylene carbonate), poly(ethylene glycol), poly(ethylene-co-vinyl alcohol), poly(glutamic acid), poly(glutamic acid-co-ethyl glutamate), poly(glycolic acid), poly(glycolide-co-trimethylene carbonate) (PGA/PTMC), poly(hydroxypropyl methacrylamide), poly(imino carbonates), poly(leucine), poly(leucine-co-hydroxyethyl glutamine), poly(L-lactide-co-D,L-lactide) (PLLA/PLA), poly(L-lactide-co-glycolide) (PLLA/PGA), poly(lysine), poly(ortho esters), poly(orthoesters), poly(oxaamides), poly(oxaesters), poly(phosphate ester), poly(phosphazene), poly(phospho esters), poly(phosphoesters), poly(propylene carbonate), poly(propylene glycol), poly(pyrrole), poly(tert-butyloxy-carbonylmethyl glutamate), poly(tetramethylene glycol), poly(trimethylene carbonate), poly(ureas), poly(urethanes), poly(urethaneureas), poly(vinyl alcohol), poly(vinyl alcohol-co-vinyl acetate), poly(vinylpyrrolidone) (PVP), poly[(97.5% dimethyl-trimethylene carbonate)-co-(2.5% trimethylene carbonate)], polyacrylic acid, polyalkylene oxides, polyamides, polycaprolactone (PCL) poly-(hydroxybutyrate-co-hydroxyvalerate) copolymer (PHBV), polycaprolactone (PCL), polycaprolactone co-butylacrylate, polydepsipeptides, polydioxanone (PDS), polyesters, polyethylene glycol, polyethylene oxide (PEO), polyethylene terephthalate (PET), polyglycolic acid and copolymers and mixtures thereof such as poly(L-lactide) (PLLA), polyglycolic acid [polyglycolide (PGA)], polyhydroxybutyrate (PHBT) and copolymers of polyhydroxybutyrate, polyiminocarbonates, polylactic acid, polymethacrylic acid, polyolefins, polyphosphazene polymers, polypropylene fumarate, polysaccharides such as hyaluronic acid, polytetrafluoroethylene (PTFE Teflon®), polyurethanes, silicones, tyrosine-derived polyarylates, tyrosine-derived polycarbonates, tyrosine-derived polyiminocarbonates, tyrosine-derived polyphosphonates, urethanes, and combinations, derivatives and mixtures thereof.

Exemplary erodible or bioerodible polymers that can be used for making the device include erodible or bioerodible forms of polyamide, aliphatic polycarbonates, polyalkylcyanoacrylate, polyalkylene oxalates, polyanhydride, polycarboxylic acid, polyester, poly(hydroxybutyrate), polyimide, poly(iminocarbonate), polycaprolactone (PCL), poly-D,L-lactic acid (DL-PLA), polydioxanone, poly(glycolic acid), poly-L-lactic acid (L-PLA), poly-L-lactic acid-co-glycolic acid (PLGA), polyorthoester, polyphosphazenes, and polyphosphoester, poly(trimethylene carbonate), and derivatives and mixtures thereof. The polymer may also be formed from a material selected from the group consisting of cellulose ester, polybutylene terephthalate, polycarbonate, polyester, polyether ether ketone, polyethylene-co-tetrafluoroethylene, polymethylmethacrylate, polyolefin, polypropylene, polysulfones, polytetrafluoroethylene, polyurethane, polyvinylchloride, polyvinylidene fluoride, silicone, and derivatives and combinations thereof.

Additional representative examples of the polymer for use in the invention include, but are not limited to, ABS resins, acrylic polymers and copolymers, acrylonitrile-styrene copolymers, alkyd resins, and carboxymethyl cellulose, and ethylene-vinyl acetate copolymers, cellophane, cellulose butyrate, cellulose acetate butyrate, cellulose acetate, cellulose ethers, cellulose nitrate, cellulose propionate, copolymers of vinyl monomers with each other and olefins, ethylene-methyl methacrylate copolymers, epoxy resins, ethylene vinyl alcohol copolymer (commonly known by the generic name EVOH or by the trade name EVAL), poly(glyceryl sebacate), poly(glycolic acid-co-trimethylene carbonate), poly(hydroxybutyrate-co-valerate), poly(hydroxyvalerate), poly(lactide-co-glycolide), poly(propylene fumarate), poly(trimethylene carbonate), polyacrylonitrile, polyamides, such as Nylon 66 and polycaprolactam, polycarbonates, polycyanoacrylates, polydioxanone, polyesters, polyethers, polyimides, polyisobutylene and ethylene-alphaolefin copolymers, polyoxymethylenes, polyphosphoester urethane, polyvinyl ketones, polyvinyl aromatics, such as polystyrene, polyvinyl esters, such as polyvinyl acetate, polyvinyl ethers, such as polyvinyl methyl ether, polyvinylidene halides, such as vinylidene fluoride based homo- or co-polymer under the trade name Solef™ or Kynar™, for example, polyvinylidene fluoride (PVDF) or poly(vinylidene-co-hexafluoropropylene) (PVDF-co-HFP) and polyvinylidene chloride, rayon, rayon-triacetate, silicones, vinyl halide polymers and copolymers, such as polyvinyl chloride, copolymers of these polymers with poly(ethylene glycol) (PEG), or combinations thereof.

In some embodiments, the polymer can be copolymers of poly(lactic) and glycolic acid, poly(anhydrides), poly(D,L-lactic acid), poly(D,L-lactide), poly(D,L-lactide-co-glycolide), poly(ethylene carbonate), poly(glycolic acid), poly(glycolide), poly(L-lactic acid), poly(L-lactide), poly(L-lactide-co-glycolide), poly(ortho esters), poly(oxaamides), poly(oxaesters), poly(phosphazenes), poly(phospho esters), poly(phosphoesters), poly(propylene carbonate), poly(trimethylene carbonate), poly(tyrosine derived carbonates), poly(tyrosine derived iminocarbonates), poly(tyrosine derived arylates), copolymers of these polymers with poly(ethylene glycol) (PEG), or combinations thereof.

Examples of non-bioerodible polymers useful in the present invention include poly(ethylene-co-vinyl acetate) (EVA), polyvinylalcohol and polyurethanes, such as polycarbonate-based polyurethanes.

A preferred polymer for the devices is ethyl vinyl acetate (EVA).

Either the core or any layer of the device can comprise a single type of polymer or a mixture of two or more polymers. A mixture of two polymers may modulate the release rate of the drug. It is desirable that an effective therapeutic amount of the drug be released from the device for a reasonably long period of time. U.S. Pat. No. 6,258,121 to Yang et al. disclosed a method of altering the release rate by blending two polymers with differing release rates and incorporating them into a single layer; this technique can also reduce burst release of drug upon implant.

Exemplary Pharmaceutical Substances for Use as the Core-Layer Pharmaceutical Substance, First-Layer Pharmaceutical Substance, and Additional Pharmaceutical Substances As used herein, a "drug" or "pharmaceutical substance" is any biologically active agent or other substance that has therapeutic value to a living organism, including without limitation anti-thrombotics, anticancer agents, anticoagulants, anti-platelet agents, thrombolytics, anti-proliferatives, anti-inflammatories, agents that inhibit restenosis, smooth muscle cell inhibitors, antibiotics, heparin, and the like, and/or mixtures thereof and/or any substance that may assist another substance in performing the function of providing therapeutic value to a living organism. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes.

Additional pharmaceutical substances which can be incorporated into the device include those listed in the Physicians' Desk Reference, 57th Edition (2003), including allergens, amebicides and trichomonacides, amino acid preparations, analeptic agents, analgesics, analgesics/antacids, anesthetics, anorexics, antacids, antihelmintics, antialcohol preparations, anti-allergics, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, anti-fibrin, antifibrinolytic agents, antifibrotics (systemic), antiflatulents, antifungal agents, antigonadotropin, antihistamines, antihyperammonia agents, anti-inflammatory agents, antimalarials, antimetabolites, anti-migraine preparations, antinauseants, antineoplastics, anti-obesity preparations, antiparasitics, anti-parkinsonism drugs, antiplatelet, antipruritics, antipyretics, anti-scarring, antispasmodics and anticholinergics, anti-thrombotics, antitoxoplasmosis agents, antitussives, antivertigo agents, antiviral agents, bismuth preparations, bone metabolism regulators, bronchial dilators, calcium preparations, cardiovascular preparations, central nervous system stimulants, chelating agents, choleretics, cholesterol reducers and anti-hyperlipemics, colonic content acidifiers, cough and cold preparations, decongestants, expectorants and combinations, diuretics, enzymes and digestants, fertility agents, fluorine preparations, galactokinetic agents, germicides, hematinics, histamine receptor antagonists, hormones, hydrocholeretics, hyperglycemic agents, hypnotics, immunosuppressives, mucolytics, muscle relaxants, narcotic antagonists, narcotic detoxification agents, ophthalmological osmotic dehydrating agents, otic preparations, oxytocics, parasympatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, vaginal therapeutics and vitamins and other dietary supplements, and each specific compound or composition listed under each of the foregoing categories in the Physicians' Desk Reference.

In another embodiment, the core pharmaceutical substance (if present), first-layer pharmaceutical substance, and additional pharmaceutical substances are independently selected from the group consisting of: 5-alpha-reductase inhibitors, analeptic agents, analgesics, angiotensin converting enzyme, anticancer agents, anticancer preparations, anticholinergic drug inhibitors, anticoagulants, anticonvulsants, antidepressants, antidiabetic agents, antienuresis agents, anti-inflammatory agents, anti-obesity preparations, antiparasitics, anti-parkinsonism drugs, anti-platelet agents, anti-psychotics, antispasmodics and anticholinergics, antithrombotics, antiviral agents, bronchial dilators, calcium channel blockers, central nervous system stimulants, cholesterol reducers and anti-hyperlipemics, diuretics, dopamine agonists, histamine H receptor antagonists, hormones, steroid hormones, peptide hormones, thyroid hormones, hormone mimetics, mimetics of steroid hormones, mimetics of peptide hormones, mimetics of thyroid hormones, hyperglycemic agents, immunosuppressives, narcotic antagonists, narcotic detoxification agents, ophthalmological osmotic dehydrating agents, respiratory stimulants, restenosis-inhibiting agents, sympatholytics, thyroid preparations, and uricosuric agents.

In another embodiment, the core pharmaceutical substance (if present), first-layer pharmaceutical substance, and additional pharmaceutical substances are independently selected from the group consisting of analeptic agents, analgesics, anticancer preparations, anticholinergic drug inhibitors, anticoagulants, anticonvulsants, antidepressants, antidiabetic agents, antienuresis agents, anti-inflammatory agents, anti-obesity preparations, antiparasitics, anti-parkinsonism drugs, antispasmodics and anticholinergics, antithrombotics, antiviral agents, bronchial dilators, central nervous system stimulants, cholesterol reducers and anti-hyperlipemics, diuretics, histamine H receptor antagonists, hormones, hyperglycemic agents, immunosuppressives, narcotic antagonists, narcotic detoxification agents, ophthalmological osmotic dehydrating agents, respiratory stimulants, sympatholytics, thyroid preparations, and uricosuric agents.

In another embodiment, the core pharmaceutical substance (if present), first-layer pharmaceutical substance, and additional pharmaceutical substances are independently selected from the group consisting of hormones, growth factors, angiopeptin, angiotensin converting enzyme inhibitors, captopril, cilazapril, and lisinopril.

In another embodiment, the core pharmaceutical substance (if present), first-layer pharmaceutical substance, and additional pharmaceutical substances are independently selected from the group consisting of analeptic agents, analgesics, anticancer preparations, anticholinergic drug inhibitors, anticoagulants, anticonvulsants, antidepressants, antidiabetic agents, antienuresis agents, anti-inflammatory agents, anti-obesity preparations, antiparasitics, anti-parkinsonism drugs, antispasmodics and anticholinergics, antithrombotics, antiviral agents, bronchial dilators, central nervous system stimulants, cholesterol reducers and anti-hyperlipemics, diuretics, histamine H receptor antagonists, hormones, hyperglycemic agents, immunosuppressives, narcotic antagonists, narcotic detoxification agents, ophthalmological osmotic dehydrating agents, respiratory stimulants, sympatholytics, thyroid preparations, and uricosuric agents.

Some other examples of other bioactive agents include adhesion peptides, antibodies, antigens for immunization, blood clotting factors, enzymes, hormones and growth factors, inhibitors or clot dissolving agents such as streptokinase and tissue plasminogen activator, oligonucleotides such as antisense oligonucleotides and ribozymes, receptor ligands, and retroviral vectors for use in gene therapy. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an anti-allergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable. Examples include: 4-amino-2,2,6,6-tetramethylpiperidine-1-oxyl (4-amino-TEMPO), antithrombins including sodium heparin, low molecular weight heparins and heparinoids, argatroban, calcium channel blockers (such as nifedipine), colchicine, dextran, dipyridamole, D-phe-pro-arg-chloromethylketone (synthetic antithrombin), estradiol, fibroblast growth factor (FGF) antagonists, fish oil (omega 3-fatty acid), forskolin, glycoprotein IIb/IIIa platelet membrane receptor antagonist antibody, hirudin, lovastatin (an inhibitor of HMG-CoA reductase, a cholesterol lowering drug, brand name Mevacor® from Merck & Co., Inc., Whitehouse Station, N.J.), nitric oxide or nitric oxide donors, nitroprusside, phosphodiesterase inhibitors, prostacyclin and prostacyclin analogues, prostaglandin inhibitors, recombinant hirudin, serotonin blockers, steroids, super oxide dismutases, super oxide dismutase mimetic, suramin, thioprotease inhibitors, thrombin inhibitors such as Angiomax (Biogen, Inc., Cambridge, Mass.), triazolopyrimidine (a PDGF antagonist), vapiprost, and a combination thereof.

In another embodiment, the core pharmaceutical substance (if present), first-layer pharmaceutical substance, and additional pharmaceutical substances are independently selected from the group consisting of calcium channel blockers, nifedipine, and triazolopyrimidine.

Examples of anti-inflammatory agents including steroidal and non-steroidal anti-inflammatory agents include tacrolimus, dexamethasone, clobetasol, or combinations thereof.

Exemplary anticancer drugs which can be incorporated into the device include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCl, bleomycin sulfate, busulfan, buthionine sulfoximine, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, docetaxel, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bis acetamide, homoharringtonine, hydrazine sulfate, 4-hydroxyandrostenedione, hydroxyurea, idarubicin HCl, ifosfamide, interferon alpha, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel (Taxol), pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures and derivatives thereof. Additional examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin.

In another embodiment, the anticancer drug or agent is selected from the group consisting of androgens.

Exemplary anti-inflammatory drugs which may be incorporated into the device include acetaminophen (Tylenol®), acetylsalicylic acid, APHS, aspirin, betamethasone, celecoxib, choline magnesium trisalicylate, cortisone, COX-2 inhibitors, desoxycorticosterone, dexamethasone, diclofenac, diflunisal, DuP-697, etodolac, etoricoxib, fenoprofen, flosulid, fludrocortisone, fluprednisolone, flurbiprofen, glucocorticoids, hydrocortisone, ibuprofen, indomethacin, JTE-522, ketoprofen, ketorolac, L-745337, L-748780, L-761066, lumiracoxib, mefenamic acid, meloxicam, meprednisone, methylprednisolone, nabumetone (Relafen®), naproxen, nimesulide, non-steroidal anti-inflammatory drugs (NS AIDS), NS-398, oxaprosin, paramethasone, parecoxib sodium, piroxicam, prednisolone, prednisone, r-flurbiprofen, rofecoxib, RS-57067, S-2474, salicylic acid, SC-57666, SC-58125, sulindac, tenoxicam, alpha,beta, gamma-tocopherols, tocotrienols (and all their D,L and racemic isomers), tolmetin, triamcinolone, valdecoxib, and mixtures and derivatives thereof.

Exemplary anti-thrombotic agents which may be incorporated into the device include: Vitamin K antagonists such as Acenocoumarol, Clorindione, Dicumarol (Dicoumarol), Diphenadione, Ethyl biscoumacetate, Phenprocoumon, Phenindione, Tioclomarol, Warfarin; Heparin group antiplatelet aggregation inhibitors such as Antithrombin III, Bemiparin, Dalteparin, Danaparoid, Enoxaparin, Heparin, Nadroparin, Parnaparin, Reviparin, Sulodexide, Tinzaparin; other platelet aggregation inhibitors such as Abciximab, Acetylsalicylic acid (Aspirin), Aloxiprin, Beraprost, Ditazole, Carbasalate calcium, Cloricromen, Clopidogrel, Dipyridamole, Eptifibatide, Indobufen, Iloprost, Picotamide, Prasugrel, Prostacyclin, Ticlopidine, Tirofiban, Treprostinil, Triflusal; enzymatic anticoagulants such as Alteplase, Ancrod, Anistreplase, Brinase, Drotrecogin alfa, Fibrinolysin, Protein C, Reteplase, Saruplase, Streptokinase, Tenecteplase, Urokinase; direct thrombin inhibitors such as Argatroban, Bivalirudin, Dabigatran, Desirudin, Hirudin, Lepirudin, Melagatran, Ximelagatran; and other antithrombotics such as Dabigatran, Defibrotide, Dermatan sulfate, Fondaparinux, and Rivaroxaban.

In another embodiment, the anti-thrombotic agent is selected from the group consisting of Beraprost, Clopidogrel, and Iloprost.

Examples of anesthetics which may be incorporated into the device include but are not limited to: bupivacaine, lidocaine, and mepivacaine. Further examples of pharmaceutical substances which can be used in the present invention are: analgesics, acetaminophen, anesthetics, benzodiazepine antagonist flumazenil, benzodiazepine, buprenorphine, carbamazepine, clonidine, fentanyl, hydrocodone, hydromorphone, levorphanol, lidocaine, meperidine, methadone, morphine, nalbuphine, narcotics, opioids, pentazocain, propoxyphene, tramadol, trimipramine maleate, zaleplon, and derivatives, combinations and mixtures thereof.

Examples of antimicrobials which may be incorporated into the device include, but are not limited to, acetyl sulfisoxazole, alatrofloxacin mesylate, amoxicillin, ampicillin, atovaquone, azithromycin, aztreonam, carbenicillin, cefaclor, cefadroxil, cefamandole nafate, cefazolin, cefdinir, cefepime, cefixime, cefoperazone, cefotaxime, cefotetan, cefoxitin, cefpodoxime proxetil, cefprozil, ceftazidime, ceftazidime, ceftibuten, ceftizoxime, ceftriaxone, cefuroxime axetil, cefuroxime, cephalexin, cephalosporins, chlorhexidine, chlortetracycline, cilastatin, ciprofloxacin, clarithromycin, clavulanic acid, clindamycin, colistimethate, dalfopristin, dapsone, demeclocycline, dirithromycin, doxycycline, erythromycin and ethylsuccinate and stearate forms thereof, gatifloxacin, gentamycin, imipenem, levofloxacins, lincomycin, linezolide, loracarbef, meropenem, metronidazole, minocycline (or other tetracycline derivatives), moxifloxacin, neomycin, norfloxacin, ofloxacin, oxytetracycline, penicillin G benzathine, penicillin G, piperacillin, polymyxin B, quinupristin, rifabutin, rifampin, streptomycin, sulbactam, sulfacetamide, sulfamethoxazole, tetracycline, ticarcillin, tobramycin, triclosan, trimethoprim, trovafloxacin mesylate, vancomycin, and combinations, derivatives and mixtures thereof.

Examples of antifungals include amphotericin B, caspofungin acetate, ciclopirox, clotrimazole, econazole, fluconazole, flucytosine, griseofulvin, itraconazole, ketoconazole, miconazole, naftifine, pyrimethamine, terbinafin, and combinations, derivatives and mixtures thereof.

A subset of pharmaceutical substances of interest is buprenorphine, nalmefene, and dopamine agonists, such as apomorphine, lisuride, pergolide, bromocriptine, pramipexole, ropinerole, and rotigotine.

In another embodiment, the core pharmaceutical substance (if present), first-layer pharmaceutical substance, and additional pharmaceutical substances are independently selected from the group consisting of buprenorphine and fentanyl.

Kinetics of Drug Delivery

Drug delivery can have a controlled release during the life of implant. In a multi-laminate device, which comprises a core comprising a polymer and multiple layers comprising polymer and drug, the varying concentration of drug in different layers can be used to modulate the rate of drug delivery over time. In one embodiment, the device displays a generally linear release of drug over time. In another embodiment, drug release from the device is approximately constant or essentially constant over the lifetime of the device, or for a specified period within the lifetime of the device. The drug is released from the device, layer by layer, from outer-most to inner-most layers. However, each layer will have a diameter and surface area smaller than the layer outside it. Thus, layers closer to the interior will need to have a higher concentration of drug than more outer layers, in order to maintain an approximately constant or essentially constant rate of drug release. In another embodiment, the concentrations of drug layer-by-layer can be designed to create different rates of drug release. For example, if each layer contains the same or a lower drug concentration than the adjoining outer-more layer, this will result in a tapered, ever-decreasing rate of drug delivery. Modulating concentrations of drug layer-by-layer can also produce a slow rise in drug delivery over the lifetime of the implant or a specified period during the lifetime of the implant. Alternating layers of relatively high and low concentrations of drug can produce a pulsed rate of drug delivery that rises and falls over time.

The device may be designed such that the rate of drug delivery over time is determined, at least in part, by total surface area, surface area of each successive layer, varying concentrations of drug per layer, and selection of polymer(s) in the device. The resultant concentration in the blood plasma of drug delivered by the device may be at least about 0.1 ng/ml blood plasma, generally about 0.1 to about 10 ng/ml. In some embodiments, the steady state of drug is about 1 to about 10 ng/ml blood plasma. In other embodiments, the steady state plasma level of drug is about 1 to about 6 ng/ml blood plasma. In one embodiment, more than one implantable device may be inserted into a patient to achieve a desired level of drug concentration in the blood plasma. The level of drug delivery is preferably within the therapeutic range of the drug and lower than a level that might cause toxicity. In one embodiment, the device can comprise multiple drugs. In one embodiment, the multiple drugs are integrated into the device and released layer by layer to maintain steady-state levels of each drug throughout the duration of implant. In another embodiment, the drugs are distributed in varying concentrations layer by layer so that drug delivery may occur in waves, with a higher dosage of one drug released, followed by a higher dosage of another drug over time.

The device may be designed to provide a steady-state concentration of drug in the blood plasma. The device may be designed such that the resulting concentration of drug in the blood plasma remains essentially constant over extended periods of time. The device may be designed such that the resulting concentration of drug in the blood plasma remains approximately constant over extended periods of time.

Insertion and Removal of Drug Delivery Device

In one method of this invention, the device is administered by subcutaneous implantation. In various embodiments, the devices are subcutaneously implanted at a site selected from a group consisting of the upper arm, scapular region, the back, the leg and the abdomen. Before implantation, the patient may be lightly anesthetized, e.g., with isoflurane or other anesthetic known in the art, and/or may have topical, transdermal, or subcutaneous anesthetic applied at the site of implantation. A small incision can be made through the skin and a trocar inserted subcutaneously, then loaded with one implant. The stylet can be inserted to hold the implant in place and the trocar carefully removed, leaving the implant in the subcutaneous space. Each site can be sutured closed and examined later. Complications such as skin irritation, inflammation, infection or other site-specific adverse effects can be monitored and treated, e.g., with antibiotics, as needed.

In various embodiments, the device can be left in the body for up to one year or more. The period of sustained release of drug into the body is thus from about 3 months to about 1 year, or longer, e.g., at least about 3 months, at least about 6 months, at least about 9 months, at least about 12 months, at least about 15 months, at least about 18 months, at least about 21 months, or at least about 24 months or more. In some embodiments the device can be left in the body for more than 1 year. Implants may be removed from the body at the end of the treatment period, through an incision, e.g., a 3-mm incision, using forceps.

A second implant may, for example, be used to deliver a pharmaceutical substance to counteract any adverse effects caused by a drug released from a first implant.

Multiple implants may be inserted into a single patient to regulate the delivery of a single drug, or to deliver several drugs.

Buprenorphine-Containing Devices

In some embodiments of the devices, the core comprises a core polymeric material of ethylene vinyl acetate (EVA). The first layer surrounding the core is made out of EVA, and contains the substance buprenorphine.

In one aspect the invention provides an implantable device for treating opiate addiction, comprising buprenorphine and a biocompatible, nonerodible polymeric matrix in a first layer surrounding a core of a biocompatible, nonerodible polymer lacking said buprenorphine, wherein said buprenorphine is encapsulated within said matrix of the first layer, and wherein when said implantable device is implanted subcutaneously in a mammal, said buprenorphine is continuously released in vivo over a sustained period of time through pores that open to the surface of said matrix at a rate that results in a steady state plasma buprenorphine level of at least about 0.1 ng/ml, typically in the range of about 0.1 to about 70 ng/ml. In some embodiments, the steady state plasma buprenorphine level is about 0.1 to about 10 ng/ml, about 0.1 to about 5 ng/ml, about 0.1 to about 3 ng/ml, about 0.1 to about 2 ng/ml, about 0.1 to about 1 ng/ml, about 0.1 to about 0.9 ng/ml, about 0.1 to about 0.8 ng/ml, about 0.1 to about 0.7 ng/ml, about 0.1 to about 0.6 ng/ml, about 0.1 to about 0.5 ng/ml, or about 0.5 to about 1 ng/ml. In other embodiments, the steady state plasma buprenorphine level is about 1 to about 10 ng/ml, about 1 to about 6 ng/ml, about 1 to about 5 ng/ml, about 1 to about 3 ng/ml, about 1 to about 2 ng/ml, or about 1 ng/ml. In some embodiments, the polymeric matrix of both the core and the first layer comprises EVA. In some embodiments wherein the polymeric matrix of both the core and the first layer of the implantable device comprises EVA, the vinyl acetate content can be about 2 to about 40, about 10 to about 35, about 30 to about 35%, or about 33% by weight. The EVA-buprenorphine blend of the first layer of the implantable devices generally comprise about 10% to about 85%, such as about or at least about 10, 20, 30, 40, 50, 55, 60, 65, 70, 75, 80, or 85% buprenorphine, often about 50% to about 75% buprenorphine. In one embodiment, the EVA-buprenorphine blend of the first layer of the implantable device comprises about 50% buprenorphine and about 50% EVA. In another embodiment, the EVA-buprenorphine blend of the first layer of the implantable device comprises about 66.7% buprenorphine and about 33.3% EVA. In another embodiment, the EVA-buprenorphine blend of the first layer of the implantable device comprises about 75% buprenorphine and about 25% EVA. In various embodiments, the sustained period of time for buprenorphine release is from about 3 months to about 1 year, or longer, e.g., at least about 3, 6, 9, or 12 months.

In another aspect, the invention provides an implantable device for treating pain, including chronic pain or acute pain, comprising buprenorphine and a biocompatible, nonerodible polymeric matrix in a first layer surrounding a core of a biocompatible, nonerodible polymer lacking said buprenorphine, wherein said buprenorphine is encapsulated within said matrix of the first layer, and wherein when said implantable device is implanted subcutaneously in a mammal, said buprenorphine is continuously released in vivo over a sustained period of time through pores that open to the surface of said matrix at a steady state rate of at least about 0.1 mg per day, generally in the range of about 0.1 to about 5 mg per day, about 0.1 to about 4 mg per day, about 0.1 to about 3 mg per day, about 0.1 to about 2 mg per day, about 0.1 to about 1 mg per day, about 0.2 to about 5 mg per day, about 0.2 to about 4 mg per day, about 0.2 to about 3 mg per day, about 0.2 to about 2 mg per day, about 0.2 to about 1 mg per day, about 0.3 to about 5 mg per day, about 0.3 to about 4 mg per day, about 0.3 to about 3 mg per day, or about 0.3 to about 2 mg per day. In some embodiments, the steady state rate of buprenorphine release is about 0.1 mg per day, 0.2 mg per day, 0.3 mg per day, about 0.4 mg per day, about 0.5 mg per day, about 0.6 mg per day, about 0.7 mg per day, about 0.8 mg per day, about 0.9 mg per day, about 1.0 mg per day, about 1.1 mg per day, about 1.2 mg per day, about 1.3 mg per day, about 1.4 mg per day, about 1.5 mg per day, about 2 mg per day, about 3 mg per day, about 4 mg per day, about 5 mg per day, in vivo or in vitro. In some embodiments, the polymeric matrix of both the core and the first layer comprises EVA. In some embodiments wherein the polymeric matrix of both the core and the first layer implantable device comprises EVA, the vinyl acetate content can be about 2 to about 40, about 10 to about 35, about 30 to about 35%, or about 33% by weight. The EVA-buprenorphine blend of the first layer of the implantable devices generally comprise about 10% to about 85%, such as about or at least about 10, 20, 30, 40, 50, 55, 60, 65, 70, 75, 80, or 85% buprenorphine, often about 50% to about 75% buprenorphine. In one embodiment, the EVA-buprenorphine blend of the first layer of the implantable device comprises about 50% buprenorphine and about 50% EVA. In another embodiment, the EVA-buprenorphine blend of the first layer of the implantable device comprises about 66.7% buprenorphine and about 33.3% EVA. In another embodiment, the EVA-buprenorphine blend of the first layer of the implantable device comprises about 75% buprenorphine and about 25% EVA. In various embodiments, the sustained period of time for buprenorphine release is from about 3 months to about 1 year, or longer, e.g., at least about 3, 6, 9, or 12 months.

In some embodiments, the implantable device for treatment of opiate addiction or treatment of pain, such as chronic or acute pain, is produced by an extrusion process. In various embodiments, the devices are subcutaneously implanted at a site selected from the group consisting of the upper arm, the back, and the abdomen. In one embodiment, extruded devices comprise dimensions of about 2.4 mm in diameter and about 2.6 cm in length. In other embodiments, extruded devices comprise dimensions of about 2 to about 3 mm in diameter and about 2 to about 3 cm in length. In further embodiments, extruded devices comprises dimensions of about 0.5 to about 7 mm in diameter and about 0.5 to about 5 cm in length. In further embodiments, extruded devices comprises dimensions of about 0.5 to about 7 mm in diameter and about 0.5 to about 10 cm in length. In some embodiments in which extruded devices comprise dimensions of about 2.4 mm in diameter and about 2.6 cm in length, the devices each release about 1 mg buprenorphine per day in vitro.

In some embodiments of the invention, the implantable devices are administered by subcutaneous implantation. In various embodiments, the devices are subcutaneously implanted at a site selected from the group consisting of the upper arm, scapular region, the back, the leg and the abdomen.

As used herein, "buprenorphine" refers to buprenorphine free base and pharmaceutically acceptable salts thereof, such as buprenorphine HCl. Norbuprenorphine can also be used in place of buprenorphine. Incorporation of buprenorphine into the polymeric matrix causes the formation of a series of interconnecting channels and pores that are accessible to the surface for release of the drug. Where appropriate, a coating that is impermeable to the drug is placed over at least a portion of the device to further regulate the rate of release. Where appropriate, the device does not have any coating that is impermeable to the drug. When implanted subcutaneously, devices of the invention continuously release buprenorphine for an extended period of time with a pseudo or near zero order release rate. After an initial burst following implantation, release rates are typically within about 10-20% of the steady state average. In some embodiments, the initial burst of buprenorphine released in vivo after implantation is reduced or minimized by prewashing the implantable devices before implantation to remove surface buprenorphine. Prewashing may be performed in any solution in which buprenorphine is soluble, for example 30 minutes in ethanol or normal saline. The release rate can be altered by modifying the percent drug loading, porosity of the matrix, structure of the implantable device, or hydrophobicity of the matrix, or by adding a hydrophobic coating to the exterior of the implantable device. The devices can deliver buprenorphine without the need for external medical equipment such as intravenous lines or pumps.

Devices may be produced using an extrusion process, wherein ground EVA is blended with buprenorphine, melted, and extruded into rod-shaped structures. Rods are cut into individual implantable devices of the desired length, packaged, and sterilized prior to use. Other methods for encapsulating therapeutic compounds in implantable polymeric, nonerodible matrices are well known to those of skill in the art. Such methods include, for example, solvent casting (see, e.g., U.S. Pat. Nos. 4,883,666, 5,114,719, and 5,601,835). A skilled artisan would be able to readily determine an appropriate method of preparing such an implantable device, depending on the shape, size, drug loading, and release kinetics desired for a particular type of patient or clinical indication.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entirety.

What is claimed is:

1. An implantable device for delivery of a pharmaceutical substance to a patient, comprising:
    a rod-shaped core comprising a core polymeric material, wherein the core does not comprise a pharmaceutical substance, wherein the core polymeric material is ethylene vinyl acetate (EVA), and wherein the core has a diameter of about 0.5 mm to about 3.5 mm;
    a first layer comprising a first-layer pharmaceutical substance and EVA surrounding the core; and
    one or more additional layers, wherein each of the one or more additional layers comprise an independently selected additional pharmaceutical substance and EVA in a blend,
    wherein the EVA has a flexural strength when unblended with pharmaceutical substance,
    wherein the blend of the additional pharmaceutical substance and the EVA in each of the one or more additional layers has about 20% to 90% of the flexural strength of the EVA unblended with pharmaceutical substance;
    wherein the first-layer pharmaceutical substance and the additional pharmaceutical substances are the same or different;
    wherein at least one of the first-layer pharmaceutical substance and the additional pharmaceutical substances is L-triiodothyronine;
    wherein the first-layer pharmaceutical substance and the additional pharmaceutical substances are released through pores that open to the surface of the device; and
    wherein the outermost layer of the device comprises at least one of the additional pharmaceutical substances.

2. The device of claim 1, wherein the first-layer pharmaceutical substance is L-triiodothyronine.

3. The device of claim 1, wherein the first-layer pharmaceutical substance and the one or more additional pharmaceutical substances in the one or more additional layers are independently selected from the group consisting of L-triiodothyronine and L-thyroxine.

4. The device of claim 1, wherein each of the first layer and the one or more additional layers has a different average concentration of pharmaceutical substance.

5. The device of claim 4, wherein the average concentration of pharmaceutical substance in the one or more additional layers decreases with increasing distance from the core.

6. The device of claim 4, wherein the average concentration of pharmaceutical substance in the one or more additional layers increases with increasing distance from the core.

7. The device of claim 1, wherein the first-layer pharmaceutical substance is L-triiodothyronine.

8. The device of claim 7, wherein the first layer comprises about 10% to 85% L-triiodothyronine.

9. The device of claim 1, wherein the first-layer pharmaceutical substance and each of the one or more additional pharmaceutical substances are L-triiodothyronine.

10. A method for delivering a first-layer pharmaceutical substance and one or more additional pharmaceutical substances to a patient in need thereof, comprising the step of inserting a device of claim 1 subcutaneously into the patient.

11. The method of claim 10, wherein the device remains implanted in the patient for about 3 months to about 24 months.

12. The method of claim 11, wherein the concentration of pharmaceutical substance in the blood is approximately constant or essentially constant for about 3 months to about 24 months.

* * * * *